US011045523B2

(12) United States Patent
Nielsen et al.

(10) Patent No.: US 11,045,523 B2
(45) Date of Patent: Jun. 29, 2021

(54) FORMULATION OF GROWTH HORMONE ALBUMIN-BINDER CONJUGATE

(71) Applicant: Novo Nordisk Health Care AG, Zurich (CH)

(72) Inventors: Jette Nielsen, Skovlunde (DK); Marie Eskling, Holte (DK); Stina Granzau Christensen, Roskilde (DK)

(73) Assignee: NOVO NORDISK HEALTHCARE AG, Zurich (CH)

( * ) Notice: Subject to any disclaimer, the term of this patent is extended or adjusted under 35 U.S.C. 154(b) by 0 days.

(21) Appl. No.: 14/780,161

(22) PCT Filed: Apr. 4, 2014

(86) PCT No.: PCT/EP2014/056819
§ 371 (c)(1),
(2) Date: Sep. 25, 2015

(87) PCT Pub. No.: WO2014/166836
PCT Pub. Date: Oct. 16, 2014

(65) Prior Publication Data
US 2016/0058879 A1    Mar. 3, 2016

Related U.S. Application Data

(60) Provisional application No. 61/821,890, filed on May 10, 2013, provisional application No. 61/879,956, filed on Sep. 19, 2013.

(30) Foreign Application Priority Data

Apr. 5, 2013   (EP) .................................... 13162480
Sep. 18, 2013  (EP) .................................... 13184957

(51) Int. Cl.
| | |
|---|---|
| *A61K 38/27* | (2006.01) |
| *A61K 47/26* | (2006.01) |
| *A61K 47/64* | (2017.01) |
| *A61K 47/10* | (2017.01) |
| *A61K 9/00* | (2006.01) |
| *A61K 47/18* | (2017.01) |
| *A61K 47/54* | (2017.01) |
| *A61K 47/34* | (2017.01) |

(52) U.S. Cl.
CPC .............. *A61K 38/27* (2013.01); *A61K 47/26* (2013.01); *A61K 47/643* (2017.08); *A61K 9/0019* (2013.01); *A61K 47/10* (2013.01); *A61K 47/183* (2013.01); *A61K 47/34* (2013.01); *A61K 47/542* (2017.08); *A61K 47/545* (2017.08)

(58) Field of Classification Search
None
See application file for complete search history.

(56) References Cited

U.S. PATENT DOCUMENTS

| | | |
|---|---|---|
| 4,683,202 A | 7/1987 | Mullis |
| 5,045,312 A | 9/1991 | Aston et al. |
| 5,156,956 A | 10/1992 | Motoki et al. |
| 5,252,469 A | 10/1993 | Andou et al. |
| 5,438,040 A | 8/1995 | Ekwuribe |
| 5,545,618 A | 8/1996 | Buckley et al. |
| 5,646,272 A | 7/1997 | Kramer et al. |
| 5,731,183 A | 3/1998 | Kobayashi et al. |
| 5,736,356 A | 4/1998 | Sano et al. |
| 5,834,250 A | 11/1998 | Wells et al. |
| 5,849,535 A | 12/1998 | Cunningham et al. |
| 5,891,840 A | 4/1999 | Cady et al. |
| 5,951,972 A | 9/1999 | Daley et al. |
| 6,004,931 A | 12/1999 | Cunningham et al. |
| 6,057,292 A | 5/2000 | Cunningham et al. |
| 6,136,536 A | 10/2000 | Tomkinson et al. |
| 6,143,523 A | 11/2000 | Cunningham et al. |
| 6,268,343 B1 | 7/2001 | Knudsen et al. |
| 6,358,705 B1 | 3/2002 | Kjeldsen et al. |
| 6,528,486 B1 | 3/2003 | Larsen et al. |
| 6,608,183 B1 | 8/2003 | Cox, III |
| 7,132,269 B2 | 11/2006 | Lacoux |
| 7,153,930 B1 | 12/2006 | Morrison et al. |
| 8,513,192 B2 | 8/2013 | Olsen et al. |
| 8,779,109 B2 | 7/2014 | Behrens et al. |
| 8,841,249 B2 | 9/2014 | Johansen et al. |
| 8,841,252 B2 * | 9/2014 | Bjorn .................. A61K 9/0019 514/11.4 |
| 8,865,868 B2 | 10/2014 | Behrens et al. |
| 9,211,342 B2 | 12/2015 | Demuth et al. |
| 9,695,226 B2 | 7/2017 | Behrens et al. |
| 2001/0011071 A1 | 8/2001 | Knudsen et al. |
| 2002/0142964 A1 | 10/2002 | Nissen et al. |
| 2003/0125232 A1 | 7/2003 | Griffin et al. |
| 2003/0162949 A1 | 8/2003 | Cox |
| 2003/0165996 A1 | 9/2003 | Halkier et al. |

(Continued)

FOREIGN PATENT DOCUMENTS

| | | |
|---|---|---|
| CN | 1269805 A | 10/2000 |
| CN | 1867360 A | 11/2006 |

(Continued)

OTHER PUBLICATIONS

Urban J. Lewis et al "An interchain disulfide dimer of human growth hormone" Journal of Biological Chemistry, 1977, vol. 252, No. 11, pp. 3697-3702.

(Continued)

*Primary Examiner* — Christine J Saoud
(74) *Attorney, Agent, or Firm* — Jianjie Hu

(57) ABSTRACT

The present invention relates to compositions of growth hormone albumin-binder conjugates including pharmaceutical formulations. The compositions are able to provide initial and long term stability of the growth hormone albumin-binder conjugate, rendering such compositions suited for use as a pharmaceutical formulation.

2 Claims, 7 Drawing Sheets

Specification includes a Sequence Listing.

(56) References Cited

U.S. PATENT DOCUMENTS

| | | |
|---|---|---|
| 2004/0001827 A1 | 1/2004 | Dennis |
| 2004/0053370 A1 | 3/2004 | Glaesner et al. |
| 2005/0170404 A1 | 8/2005 | Cho et al. |
| 2005/0260237 A1 | 11/2005 | Byun et al. |
| 2005/0266532 A1 | 12/2005 | Rosen et al. |
| 2006/0094655 A1 | 5/2006 | Guyon et al. |
| 2006/0183197 A1 | 8/2006 | Andersen et al. |
| 2007/0105770 A1 | 5/2007 | Johansen et al. |
| 2007/0203058 A1 | 8/2007 | Lau et al. |
| 2008/0095837 A1 | 4/2008 | Dinh et al. |
| 2009/0156478 A1 | 6/2009 | Lau et al. |
| 2011/0189124 A1 | 8/2011 | Rosendahl et al. |
| 2011/0223151 A1* | 9/2011 | Behrens ........... A61K 47/48246 424/94.64 |
| 2012/0172303 A1 | 7/2012 | Johansen et al. |
| 2013/0012684 A1 | 1/2013 | Buchardt |
| 2014/0107324 A1 | 4/2014 | Behrens et al. |
| 2014/0329750 A1 | 11/2014 | Andersen et al. |
| 2017/0239362 A1 | 8/2017 | Behrens et al. |
| 2018/0221501 A1 | 8/2018 | Andersen et al. |
| 2020/0306382 A1 | 10/2020 | Andersen et al. |

FOREIGN PATENT DOCUMENTS

| | | |
|---|---|---|
| CN | 103002918 A | 3/2013 |
| CN | 103002948 A | 3/2013 |
| EA | 010626 B1 | 10/2008 |
| EP | 243929 A2 | 11/1987 |
| EP | 0458064 A2 | 11/1991 |
| EP | 534568 A2 | 3/1993 |
| EP | 555649 A2 | 8/1993 |
| EP | 785276 A1 | 7/1997 |
| EP | 950665 A1 | 10/1999 |
| EP | 1012184 A1 | 6/2000 |
| EP | 1329458 A2 | 7/2003 |
| EP | 05102171.5 | 3/2005 |
| EP | 1704165 A1 | 9/2006 |
| EP | 1941901 A1 | 7/2008 |
| JP | H07503600 A | 4/1995 |
| JP | H1156378 A | 3/1999 |
| JP | H1192499 A | 4/1999 |
| JP | 2000-500505 A | 1/2000 |
| JP | 2001510033 A | 7/2001 |
| JP | 2001521402 A | 11/2001 |
| JP | 2002-504527 A | 2/2002 |
| JP | 2002-508162 A | 3/2002 |
| JP | 2003-505347 | 2/2003 |
| JP | 2003-199569 A | 7/2003 |
| JP | 2004-528014 A | 9/2004 |
| JP | 2004-535442 A | 11/2004 |
| JP | 2005500831 A | 1/2005 |
| JP | 2009-523815 A | 6/2009 |
| JP | 2010-116407 A | 5/2010 |
| RU | 2073686 C1 | 2/1997 |
| RU | 2075509 C1 | 3/1997 |
| RU | 2006107600 A | 10/2007 |
| WO | 90/04788 A1 | 5/1990 |
| WO | 90/11296 A1 | 10/1990 |
| WO | 91/11457 A1 | 8/1991 |
| WO | 1992/05271 A1 | 4/1992 |
| WO | 92/09690 A2 | 6/1992 |
| WO | 94/03198 A1 | 2/1994 |
| WO | 94/10200 A1 | 5/1994 |
| WO | 1996/06931 A1 | 3/1996 |
| WO | 96/12505 A1 | 5/1996 |
| WO | 1996/22366 A1 | 7/1996 |
| WO | 96/29342 | 9/1996 |
| WO | 9629070 A1 | 9/1996 |
| WO | 97/11178 A1 | 3/1997 |
| WO | 97/39768 A1 | 10/1997 |
| WO | 98/08872 A1 | 3/1998 |
| WO | 9808871 A1 | 3/1998 |
| WO | 1998/38285 A2 | 9/1998 |
| WO | 99/03887 | 1/1999 |
| WO | 99/43341 | 9/1999 |
| WO | 99/43361 A1 | 9/1999 |
| WO | 99/43705 A1 | 9/1999 |
| WO | 99/43708 | 9/1999 |
| WO | 9943707 | 9/1999 |
| WO | 00/34331 | 6/2000 |
| WO | 00/69911 | 11/2000 |
| WO | 01/04156 | 1/2001 |
| WO | 01/09163 A2 | 2/2001 |
| WO | 2001/12155 A1 | 2/2001 |
| WO | 0151071 | 7/2001 |
| WO | 2001/58935 A2 | 8/2001 |
| WO | 02058725 | 1/2002 |
| WO | 02/46227 A2 | 6/2002 |
| WO | 2002/055532 A2 | 7/2002 |
| WO | 02055532 A2 | 7/2002 |
| WO | 02/087597 A1 | 11/2002 |
| WO | 02098446 A1 | 12/2002 |
| WO | 03/002136 | 1/2003 |
| WO | 2003/013573 A1 | 2/2003 |
| WO | 03/040309 A2 | 5/2003 |
| WO | 03/042245 A2 | 5/2003 |
| WO | 2003/044056 A2 | 5/2003 |
| WO | 03/087139 A2 | 10/2003 |
| WO | 2003/093465 A1 | 11/2003 |
| WO | 2004/022593 A2 | 3/2004 |
| WO | 2004/065621 A1 | 8/2004 |
| WO | 04/074315 A2 | 9/2004 |
| WO | 2004/099246 A2 | 11/2004 |
| WO | 2005/014035 A2 | 2/2005 |
| WO | 2005/014049 A2 | 2/2005 |
| WO | 2005/027978 A2 | 3/2005 |
| WO | 2005/028516 A2 | 3/2005 |
| WO | 2005/035553 A2 | 4/2005 |
| WO | 05/058958 A2 | 6/2005 |
| WO | 2005/070468 A2 | 8/2005 |
| WO | 2005/105148 | 11/2005 |
| WO | 06/005667 A2 | 1/2006 |
| WO | 2006/013202 A2 | 2/2006 |
| WO | 06/037810 A2 | 4/2006 |
| WO | 2006/048777 A2 | 5/2006 |
| WO | 2006048777 A2 | 5/2006 |
| WO | 2006071840 A2 | 7/2006 |
| WO | 06/097536 A2 | 9/2006 |
| WO | 06/097538 A1 | 9/2006 |
| WO | 2006/097537 A2 | 9/2006 |
| WO | 2006/134148 A2 | 12/2006 |
| WO | 2006/134173 A2 | 12/2006 |
| WO | 2007/020290 A1 | 2/2007 |
| WO | 2007025988 A2 | 3/2007 |
| WO | 2007/093594 A1 | 8/2007 |
| WO | 2008/003750 A2 | 1/2008 |
| WO | 2008/14430 A1 | 1/2008 |
| WO | 2008/020075 A1 | 2/2008 |
| WO | 2008/027854 A2 | 3/2008 |
| WO | 2008/101240 A1 | 8/2008 |
| WO | 2009/030771 A1 | 3/2009 |
| WO | 2010/015668 A1 | 2/2010 |
| WO | 2010/029159 A1 | 3/2010 |
| WO | 2010029107 A1 | 3/2010 |
| WO | 2010/084173 A1 | 7/2010 |
| WO | 2010/102886 A1 | 9/2010 |
| WO | 2011015649 A1 | 2/2011 |
| WO | 2011/89250 A2 | 7/2011 |
| WO | 2011089255 A1 | 7/2011 |
| WO | 2011101261 A2 | 8/2011 |

OTHER PUBLICATIONS

Hodgson et al., 2004, "The Synthesis of Peptides and Proteins Containing Non-Natural Amino Acids," Chemical Reviews 33(7):422-430.

Holz et al., 2003, "Glucagon-Like Peptide-1 Synthetic Analogs: New Therapeutic Agents for Use in the Treatment of Diabetes Mellitus," Current Medicinal Chemistry 10(22):2471-2483.

Kim et al., 2003, "Development and Characterization of a Glucagon-Like Peptide 1-Albumin Conjugate," Diabetes 52:751-759.

(56) References Cited

OTHER PUBLICATIONS

Makino et al., 2005, "Semisynthesis of Human Ghrelin: Condensation of a Boc-Protected Recombinant Peptide With a Synthetic O-Acylated Fragment," Biopolymers 79(5):238-247.
Okada, 2001, "Synthesis of Peptides by Solution Methods," Current Organic Chemistry 5(1):1-43.
Ostrovsky, 1975, "Comparative Characteristics of the Hydrophobic Nature of Certain Proteins by Their Interaction With 2-P Toluidino," Ukrayins'kyi Biokhimichnyi Zhurnal 47(6):701-707.
Picó, 1990, "Use of 1-Anilino-8-Naphthalene Sulfonate as a Reporter Molecule to Study the Bile Salts-Bovine Serum Albumin Binding," Studia Biophysica 136(1):21-26, Abstract XP-008039734.
Rudinger, 1976, "Characteristics of the Amino Acids as Components of a Peptide Hormone Sequence," Peptides Hormones, JA Parsons Edition, University Park Press, Jun. 1976, pp. 1-7.
Schinzel et al., 1991, "The Phosphate Recognition Site of *Escherichia coli* Maltodextrin Phosphorylase," Federation of European Biochemical Society Jul. 1991, 286(1, 2):125-128.
Sheffield, 2001, "Modification of Clearance of Therapeutic and Potentially Therapeutic Proteins," Current Drug Targets Cardiovascular & Haematological Disorders 1(1):1-22.
Sigma Genosys (Web Site), Designing Custom Peptides, pp. 1-2, Accessed Dec. 16, 2004.
Voet et al., 1995, Biochemistry 2nd ed., John Wiley & Sons, Inc., pp. 235-241.
Wallace, 1995, "Peptide Ligation and Semisynthesis," Current Opinion in Biotechnology 6(4):403-410.
Zobel et al., 2003, "Phosphate Ester Serum Albumin Affinity Tags Greatly Improve Peptide Half-Life in Vivo," Bioorganic & Medicinal Chemistry Letters 13:1513-1515.
Knudsen, L.B. et al., "Potent Derivatives of Glucagon-Like Peptide-1 With Pharmacokinetic Properperties Suitable for Once Daily Administration", Journal of Medicinal Chemistry, 2000 vol. 43, pp. 1664-1669.
Deacon, C.F. et al., "Dipeptidyl peptidase IV resistant analogues of glucagon-like peptide-1 which have extended metabolic stability and improved biological activity." 1998, Diabetologia, vol. 41, pp. 271-278.
Kurtzhals, P, et al., "Albumin Binding of Insulins Acylated With Fatty Acids: Characterization of the Ligand-Protein Interaction and Correlation Between Binding Affinity and Timing of the Insulin Effect in Vivo," Biochem J, 1995, vol. 312, pp. 725-731.
Watanabe et al., "Structure-Activity Relationships of Glucagon-Like Peptide-1 (7-36) Amide: Insulinotropic Activities in Perfused Rat Pancreases, and Receptor Binding and Cyclic AMP Production in RINm5F Cells," Journal of Endocrinology, 1994, vol. 140, pp. 45-52.
Jung-Guk Kim et al. Diabetes Development and Characterization of a Glucagon-Like Peptide 1-Albumin Conjugate/ The Ability to Activate the Glucagon-Lile Peptide 1 Receptor in Vivo 2003 52-751-759.
Definition of Moiety, From http://dictionary.reference.com/browse/moiety, pp. 1-2. Accessed Aug. 26, 2010.
Small Bowel Syndrome from e-Medicine, pp. 1-12, Accessed Sep. 24, 2008.
Alam K S M et al, Journal of Biotechnology, "Expression and Purification of a Mutant Human Growth Hormone That is Resistant to Proteolytic Cleavage by Thrombin, Plasmin and Human Plasma in Vitro", 1998, vol. 65, No. 2-3, pp. 183-190.
Chantalet L et al, Protein and Peptide Letters, "The Crystal Structure of Wild-Type Growth Hormone at 2.5A Resolution", 1995, vol. 2, No. 2, pp. 333-340.
Carey et al, The Liver: Biology and Pathobiology 2nd Edition, Raven Press Ltd, "Enterohepatic Circulation", 1988, vol. 33, pp. 573-616.
Devos A. M. et al, Science, "Human Growth Hormone and Extracelleular Domain of Its Receptor: Crystal Structure of the Complex", 1992, vol. 255, pp. 306-312.

Garcia-Barros,et al, Journal of Endocrinology, "Proteolytic Processing of Human Growth Hormone (GH)by Rat Tissues in Viitro: Influence of Sex and Age", 2000, vol. 23, pp. 748-754.
Lewis.U.J, Annual Review of Physiology, "Variants of Growth Hormone and Prolactin and Their Posttranslational Modifications", 1984, vol. 46, pp. 33-42.
Lu, X et al. J. Nucl. Med. Antisense DNA delivery in vivo: liver targeting by receptor-mediated uptake. 1994. vol. 35(2). pp. 269-275.
Holzinger, F et al. Hepatology. "Fluorescent bile acid derivatives: Relationship between chemical structure and hepatic and intestinal transport in the rat." 1997. vol. 26. pp. 1263-1271.
Taniyama Y. et al. "Evidence for intramolecular disulfide bond shuffling in the folding of mutant human lysozyme." Journal of Biological Chemistry 1991, vol. 266 No. 10 pp. 6456-6461.
Sahin-Toth M et al. "Cysteine scanning mutagenesis of the N-terminal 32 amino acid residues in the lactose permease of *Escherichia coli*." Protein Science, 1994, vol. 3, p. 240-247.
Takahashi Y, Chihara K. "Short stature by mutant growth hormones", Growth Hormone & IGF Research, 1999,vol. 9: pp. 37-41.
V.M. Stepanov, "Molecular biology. Protein structure and function", Moscow, Nauka, 2005, pp. 61-62.
Ghuman J. et al., Structural basis of the drug-binding specificity of human serum albumin, Journal of Molecular Biology, 2005, vol. 353, No. 1, pp. 38-52.
Masuda.N,et al Biochimica et Biophysica Acta Molecular Cloning of CDNA Encoding 2O KDA Variant Human Growth Hormone and the Alternative Splicing Mechanism 1988 949 1 125-131.
Matthes,et al EMBO Journal Simultaneous Rapid Chemical Synthesis of Over 100 Oligonucleotides on a Microscale 1984 3 4 801-805.
Needeleman,et al—Journal of Molecular Biology—a General Method Applicable to the Search for Similarities in the Amino Acid Sequence of Two Proteins—1970, 48—pp. 443-453.
Palmberger.et al European Journal of Pharmaceutics and Biopharmaceutics : Official Thiolated Polymers: Evaluation of the Influenece of the Amount of Covalently Attached L-Cysteine to Poly(Acrylic Acid) 2007 66-405-412.
Partlow.K.C.et al Biomaterials Exploiting Lipid Raft Transport With Membrane Targeted Nanoparticles:A Strategy for Cytosolic Drug Delivery 2008 29-3367-3375.
Petersen,et al Protein Engineering Amino Acid Neighbours and Detailed Conformational Analysis of Cysteines in Proteins 1999 12 7 535-548.
S.Y.Chae,et al Bioconjugate Chemistry Preparation, Characterization and Application of Biotinylated and Biotin-Pegylated Glucagon-Like Peptide-1 Analogues for Enhanced Oral Delivery 2008 19-334-341.
Said, Hamid M; Mohammed, Zainab M. Current Opinion in Gastroenterology Intestinal Absorption of Watersoluble Vitamins: An Update 2006 22 2 140-146.
Saiki,et al Science Primer-Directed Enzymatic Amplification of DNA With a Thermostable DND Polymerase 1988 239 4839 487-491.
Takatsuka.et al European Journal of Pharmaceutics and Biopharmaceutics : Official Enhancement of Intestinal Absorption of Poorly Absorbed Hydrophilic Compounds by Simultaneous Use of Mucolytic Agent and Non-Ionic Surfacant 2006 62-52-58.
Von Heijne.G—Academic Press—Sequence Analysis of Molecular Biology: Treasure Torve or Trivial Pursuit—1987—pp. 186-188.
Zhiwen Zhang et al, Science, A New Strategy for the Synthesis of Glycoproteins, 2004 vol. 303, pp. 371-373.
Szente et al., "Solubilization of Fatty Acids and Similar Lipids by Methylated Cyclodextrins," Proceedings of the International Symposium on Cyclodextrins, Jan. 1, 1992, pp. 340-344.
Szejtli, Jozsef, Cyclodextrin Technology (a book), Published by Springer, 1988, p. 271.
Dennis, MS et al., Journal of Biological Chemistry, "Albumin Binding as a General Strategy for Improving the Pharmacokinetics of Proteins", 2002, vol. 277, No. 28 pp. 35035-35043.
Pasut, G et al., Expert Opinion on Therapeutic Patents, "Protein, Peptide and Non-Peptide Drug Pegylation . . . " 2004, vol. 14, No. 6, pp. 859-894.

(56) References Cited

OTHER PUBLICATIONS

Bebernitz et al., Journal of Medicinal Chemistry, "Reduction in Glucose Levels in STZ Diabetic Rats by 4-(2,2-Dimethyl-1-Oxopropyl) Benzoic Acid: A Prodrug Approach for Targeting the Liver" 2001 vol. 44 pp. 512-523.
Beljaars et al., Journal of Drug Targeting, "Neoglyco-and Neopeptide Albumins for Cell-Specific Delivery of Drugs to Chronically Diseased Livers" 2001 vol. 115 pp. 189-240.
Biessen et al., Journal of Medicinal Chemistry, "Synthesis of Cluster Galactosides With High Affinity for the Hepatic Asialoglycoprotein Receptor" 1995 vol. 38 Part 9 pp. 1538-1546.
Hatori et al., Journal of the Controlled Release, "Controlled Biodistribution of Galactosylated Liposomes and Incorporated Probucol in Hepatocyte-Selective Drug Targeting" 2000 vol. 69 pp. 369-377.
Kim et al., Journal of Drug Targeting, "Evaluation of the Bile Acid Transporter in Enhancing Intestinal Permeability to Renininhibitory Peptides" 1993 vol. 1 pp. 347-359.
Kramer et al., Journal of Biological Chemistry, "Liver-Specific Drug Targeting by Coupling to Bile Acids", 1992 vol. 267 Part 26 pp. 18598-18604.
Kramer et al., Journal of the Controlled Release, "Modified Bile Acids as Carriers for Peptides and Drugs", 1997 vol. 46 Part 1-2 pp. 17-30.
Kramer et al., Journal of Biological Chemistry, "Intestinal Absorption of Peptides by Coupling to Bile Acids" 1994 vol. 269 Part 14 pp. 10621-10627.
Kullack-Ublick et al., Gastroenterology, "Chlorambucil-Taurocholate is Transported by Bile Acid Carriers Expressed in Human Hepatocellular Carcinomas" 1997, vol. 113 pp. 1295-1305.
Leeson et al., Journal of Medicinal Chemistry, "Selective Thyromimetics. Cardiac-Sparing Thyroid Hormone Analogues Containing 3'-Arylmet HYL Substituents" 1989 vol. 32 Part 2 pp. 320-326.
Nezasa et al., Drug Metabolism and Disposition, "Liver-Specific Distribution of Rosuvastatin in Rats: Comparison With Pravastatin and Simvastatin" 2002 vol. 30 Part 11 pp. 1158-1163.
Pecher et al., Biophysical Chemistry, "The Effect of Additional Disulfide Bonds on the Stability and Folding of Ribonuclease" 2009 vol. 141 Part 1 pp. 21-28.
Starke et al., Bioorganic & Medicinal Chemistry Letters, "Bile Acid-Oldigodeoxynucleotide Conjugates: Synthesis and Liver Excretion in Rats", 2001 vol. 11 pp. 945-949.
Swaan, PW et al., Bioconjugate Chemistry, "Enhanced Transepithelial Transport of Peptides by" 1997 vol. 8 Part 4 pp. 520-525.
Wess et al., Tetrahedron Letters, "Modified Bile Acids: Preparation of 7A, 12A-Dihydroxy-3a-and 7A, L2A-Dihydroxy-3A-(2-Hydroxyethoxy)-SIJ-Cholanic Acid and Their Biological Activity" 1992, vol. 33 Part 2 pp. 195-198.
Inflammatory Bowel Disease from e-Medicine, pp. 1.24, Accessed Sep. 24, 2008.
Ngo JT et al., "Computational Complexity, Protein Structure Prediction, and the Levinthal Paradox," The Protein Folding Problem and Tertiary Structure Prediction, K. Mere Jr. and S. LeGrand Edition, 1994, pp. 433-495.
Residue definition from www.dictionary.com, pp. 1-6, Accessed May 5, 2009.
Green, Brian D. et al Biological Chemistry. Degradation, Receptor Binding, Insulin . . . 2004 385 2 169-177.
Greenwald Journal of the Controlled Release PEG Drugs: An Overview 2001 74-159-171.
Ji, J. et al. Biomaterials Stearyl Poly (Ethylene Oxide) Grafted Surfaces for Preferential Adsorption of Albumin. 2001 22-3015-3023.
Knudsen, L.B. Journal of Medicinal Chemistry Glucagon-Like Peptide-1 . . . 2004 47-4128-4134.
Simonovsky et al. Journal of Biomaterials Science, Polymer Edition Poly(Ether Urethane)S Incorporating Long Alkyl Side-Chains With Terminal Carboxyl Groups as Fatty Acid Mimics: Synthesis,Structural Characterization and Protein Adsorption 2005 16 12 1463-1483.
Soltero and Ekwurlbe Innovations in Pharmaceutical Technology the Oral Delivery of Protein and Peptide Drugs. 2001 1-106-110.
Still, J. Gordon, Diabetes/Metabolism Research Reviews, Development of Oral Insulin: Progress and Current Status, 2002, vol. 18, Suppl 1, pp. S29-S37.
Veronese F. M Biomaterials Peptide and Protein Pegylation: A Review of Porblems and Solutions 2001 22 5 405-417.
English abstract of JP 2004535442.
English abstract of RU 2006107600.
English abstract of JP 2010116407.
English abstract of JP 2004528014.
Berendsen, 1998, "A Glimpse of the Holy Grail?" Science 282:642-643.
Bradley et al., 2002, "Limits of Cooperativity in a Structurally Modular Protein: Response of the Notch Ankyrin Domain to Analogous Alanine Substitutions in Each Repeat," Journal of Molecular Biology 324:373-386.
Chuang et al., 2002, "Pharmaceutical Strategies Utilizing Recombinant Human Serum Albumin," Pharmaceutical Research 19(5):569-577.
Han, 2002, "Targeted Prodrug Design to Optimize Drug Delivery," AAPS Pharmsci 2(1):1-11.
Chou D. K. et al., Effects of Tween 20 (R) and Tween 80 (R) on the stability of albutropin during agitation, Journal of Pharmaceutical Sciences, American Pharmaceutical Association, Washington, US, 2005, vol. 94, No. 6, pp. 1368-1381.
Osborn B. L. et al., Albutropin: a growth hormone-albumin fusion with improved pharmacokinetics and pharmacodynamics in rats and monkeys, European Journal of Pharmacology, Elsevier Science, NL, 2002, vol. 456, No. 1-3, pp. 149-158.
Poznansky M. J. et al., Growth hormone-albumin conjugates Reduced renal toxicity and altered plasma clearance, FEBS Letters, Elsevier, Amsterdam, NL, 1988, vol. 239, No. 1, pp. 18-22.
Katakam M. et al., Use of Poloxamer Polymers to Stabilize Recombinant Human Growth Hormone Against Various Processing Stresses, Pharmaceutical Development and Technology, New York, NY, US, 1997, vol. 2, No. 2, pp. 143-149.
Bam N. B. et al.,Tween protects recombinant human growth hormone against agitation-induced damage via hydrophobic interactions, Journal of Pharmaceu Tical Sciences, American Pharmaceutical Association, Washington, 1998, US, vol. 87, No. 12, pp. 1554-1559.
Katakam M. et al., Effect of Surfactants on the Physical Stability of Recombinant Human Growth Hormone, Journal of Pharmaceutical Sciences, American Pharmaceutical Association, Washington, US, 1995, vol. 84, No. 6, pp. 713-716.
Filikov et al, "Computational Stabilization of Human Growth Hormone," Protein Science, 2002, vol. 11, No. 6, pp. 1452-1461.
Kasimova, MR et al., "NMR Studies of the Bacbone Flixibility and Structure of Human Growth Hormone: A Comparison of High and Low PH Conformations," Journal of Molecular Biology, 2002, vol. 318, pp. 679-695.
Frostell-Karlsson et al., Journal of Medicinal Chemistry, "Albumin Binding Property", 2000, vol. 43, No. 10, pp. 1986-1992.
Berge et al., Journal of Pharmaceutical Sciences, "Pharmaceutical Salts", 1977, vol. 66, No. 1, pp. 1-19.
Masters, "Applications of Spray Drying," in Spray-Drying Handbook (5.sup.th ed; Longman Scientific and Technical), pp. 491-676 (1991).
Manning M.C., -, "Stability of Protein Pharmaceuticals", Pharmaceutical Research. 1989, vol. 6(11): pp. 903-918.
Altschul et al, -, "Blast Manual" downloaded Jan. 10, 2013.
Altschul et al., Journal of Molecular Biology., "BLASTP, BLASTN, and FASTA", 1990, vol. 215, No. -, pp. 403-410.
B. Lee and F.M. Richards, Journal of Molecular Biology, "The Interpretation of Protein Structures: Estimation of Static Accessibility", 1971, vol. 55, No. -, pp. 379-400.
B. Peschke et al., Bioorganic & Medicinal Chemistry, "C-Terminally Pegylated Hgh Derivatives", 2007, vol. 15, No. -, pp. 4382-4395.
Broadhead et al., Drug Delivery, "The Spray Drying of Pharmaceuticals", 1992, vol. 18, No. 11 & 12, pp. 1169-1206.

(56) References Cited

OTHER PUBLICATIONS

C. A. Lipinski et al., Advanced Drug Delivery Reviews, "Experimental and Computational Approaches to Estimate Solubility and Permeability in Drug Discovery and Development Settings", 1997, vol. 23, pp. 3-25.
Carpenter and Crowe, Cryobiology, "Modes of Stabilization of a Protein by Organic Solutes During Dessication", 1988, vol. 25, No. -, pp. 459-470.
Dayhoff et al., A Model of Evolutionary Change in Protiens, "Atlas of Protein Sequence and Structure", 1978, vol. 5, No. 3, pp. 345-352.
G. T. Hermanson, -, "Bioconjugate Techniques, Elsevier", 2008, vol. 2, No. -, pp. -.
I. Moriguchi, S. Hirano, I. Nakagome, H. Hirano, Chemical & Pharmaceutical Bulletin, "Comparison of Reliability of LOGP Values for Drugs Calculated by Several Methods", 1994, vol. 42, No. -, pp. 976-978.
Kaempfer, Journal of General Microbiology, "Genus *Streptomyces*", 1991, vol. 137, No. -, pp. 1831-1892.
M. M. Kurfurst, Analytical Biochemistry, "-", 1992, vol. 200(2), No. -, pp. 244-248.
Mumenthaler et al.,, Pharmaceutical Research, "Feasibility Study on Spray-Drying Protein Pharmaceuticals: Recombinant Human Growth Hormone and Tissue-Type Plasminogen Activator", 1994, vol. 11, No. 1, pp. 41263.
Chene, N., "Growth hormones. II. Structure-function relationships," Reprod. Nutr. Dev., 1989. , 29 1-25.
Roser, Biopharmaceutical, "Trehalsoe Drying: A Novel Replacement for Freeze Drying", 1991, vol. 4, No. -, pp. 47-53.
Sato, H, Advanced Drug Delivery Reviews, "Enzymatic Procedure for Site-Specific Pegylation of Proteins", 2002, vol. 54, No. -, pp. 487-504.
T. Fujita; J. Iwasa and C. Hansch, Journal of the American Chemical Society, "A New Substituent Constant, PI, Derived From Partition Coefficients", 1964, vol. 86, No. -, pp. 5175-5180.
Wada, E et al., Biotechnology Letters, "Enzymatic Modification of . . . ", 2001, vol. 23, No. -, pp. 1367-1372.
Williams and Polli, Journal of Parenteral Science & Technology, "The Lyophilization of Pharmaceuticals: A Literature Review", 1984, vol. 38, No. 2, pp. 48-59.
Gregory J. Russel-Jones and David H. Alpers, Membrane Transporters as Drug Targets, 1999, Chapter 17, New York.
Alexander Deitrs,et al, Journal of the American Chemical Society, "Adding Amino Acids With Novel Reactivity to the Genetic Code of *Saccharomyces cerevisiae*", 2003, vol. 125, 39, pp. 11782-11783.
Altschul SF, Madden TL, Schaffer AA, Zhang J, Zhang Z, Miller W, Lipman DJ. Gapped BLAST and PSI-BLAST: a new generation of protein database search programs. Nucleic Acids Res. Sep. 1, 1997;25(17):3389-402.
Beaucage&CaruthersTetrahedron Lettersdeoxynucleoside Phosphoramidites—A New Class of Key Intermediates for Deoxypolynucleotide Synthesis 1981. vol. 22, No. 20, pp. 1859-1862.
Cabrita,et al, Biotechnology Annual Reviewprotein Expression and Refolding—A Practical Guide to Getting the Most Out of Inclusion Bodies, 2004, vol. 10, pp. 31-50.
Carillo,et al, Journal of Applied Mathametics "The Multiple Sequence Alignment Problem in Biology" 1988 vol. 48 Part 5 pp. 1073-1082.

Chalasani et al, Journal of the Controlled Releasea Novel Vitamin B12-Nanosphere Conjugate Carrier System for Peroral Delivery of Insulin, 2007, vol. 117, pp. 421-429.
Chin et al, Science, An Expanded Eukaryotic Genetic Code, 2003, vol. 301,pp. 964-967.
De Vas, A.M.et al Science—Human Growth Hormone and Extracellular Domain of Its Receptor: Crystal Structure of the Complex—1992—vol. 255—pp. 306-312.
Devereux et alNucleic Acids Researcha Comprehensive Set of Sequence Analysis Programs for the VAX, 1984, vol. 12, No. 1, pp. 387-395.
Dombkowski A, Bioinformatics, Disulfide by Design:A Computational Method for the Rational Design of Disulfide Bonds in Proteins, 2003, vol. 19, No. 14, pp. 1852-1853.
Greene, et al Protective Groups in Organic Chemistry Synthesis Protective Groups in Organic Synthesis 2006 9-0-471.
M. Gribskov, J. Devereux, Sequence Analysis Primer, Stockton Press, NewYork and Macmillan, Basingstroke (1991), pp. 90-157.
Griffin,et al Humana Press, Totowa New Jersey "Methods in Molecular Biology, vol. 24: Computer Analysis of Sequence Data Part I" 1994.
Gumbleton.M, Advanced Drug Delivery Reviews, Caveolae as Potential Macromolecule Trafficking Compartments Within Alveolar Epithelium, 2001, vol. 49, No. 3, pp. 281-300.
H.Li & Z.M.Qian, Medicinal Research Reviews. Transferrinttransferrin Receptor-Mediated Drug Delivery, 2002, vol. 22, No. 3, pp. 225-250.
Henikoff,et al Proceedings of the National Academy of Sciences of the USA Amino Acid Substitution Matrices Form Protein Blocks 1992, vol. 89, pp. 10915-10919.
Kondoh.et al, Molecular Pharmacology, a Novel Strategy for the Enhancement of Drug Absorption Using a Claudin Modulator, 2005 vol. 67, No. 3, pp. 749-756.
Lee et al, Biotechnology and Applied Biochemistry, Expression and Characterization of Human Growth Hormone-FC Fusion Proteins for Transcytosis Induction, 2007, vol. 46, pp. 211-217.
Lei Wang,et al, Science, Expanding the Genetic Code of *Escherichia coli*, 2001, vol. 292, pp. 498-500.
Leitner.V.M.et al European Journal of Pharmaceutics and Biopharmaceutics : Official Thiolated Ploymers: Evidence for the Formation of Disulphide Bonds With Mucus Glycoproteins 2003 56-207-214.
Lesk.A.M—Oxford University Press—Computational Molecular Biology: Sources and Methods for Sequence Analysis—1988—pp. 247-255.
Leuben.H.L.et al International Journal of Pharmaceutics Mucoadhesive Polymers in Personal Peptide Drug Delivery.V.Effect of Poly(Acrylates)on the Enzymatic of Peptide Drugs by Intestinal Brush Border Membrane Vesicles 1996, vol. 141, Nos. 1-2, pp. 39-52.
Liang & Young, Biochemical and Biophysical Research Communications, Insulin-Cell Penetrating Peptide Hybrids With Improved Intestinal Absorption Efficiency, 2005, vol. 335, pp. 734-738.
Lueben.H.L.et al Pharmaceutical Research Mucoadhesive Polymers in Peroral Peptide Drug Delivery .VI.Carbomer and Chitosan Improve the Intestinal Absorption of the Peptide Drug Buserelin in Vivo, 1996, vol. 13, No. 11, pp. 1668-1672.
Bekale et al., "The Role of Polymer Size and Hydrophobic End-Group in PEG-Protein Interaction," Colloids and Surfaces, B, Biointerfaces, Elsevier, Amsterdam, NL, vol. 130, Mar. 28, 2015, pp. 141-148.

* cited by examiner

A

B

A

B

Fig. 5 – continued
C
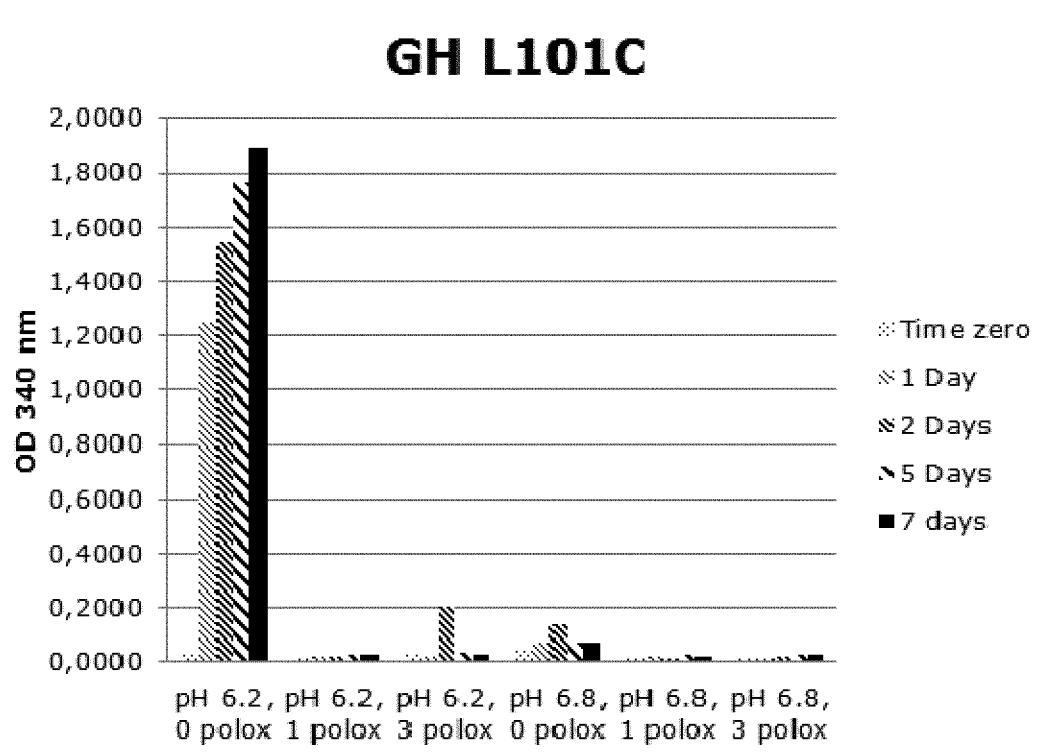

A

B

SEQUENCE LISTING

<160> NUMBER OF SEQ ID NOS: 1

<210> SEQ ID NO 1
<211> LENGTH: 191
<212> TYPE: PRT
<213> ORGANISM: Homo sapiens

<400> SEQUENCE: 1

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

FORMULATION OF GROWTH HORMONE ALBUMIN-BINDER CONJUGATE

CROSS-REFERENCE TO RELATED APPLICATIONS

This application is a 35 U.S.C. § 371 National Stage application of International Application PCT/EP2014/056819 (published as WO 2014/166836, filed Apr. 4, 2014, which claimed priority of European Patent Applications 13162480.1, filed Apr. 5, 2013 and 13184957.2, filed Sep. 18, 2013; this application claims priority under 35 U.S.C. § 119 of U.S. Provisional Applications 61/821,890, filed May 10, 2013 and 61/879,956, filed Sep. 19, 2013, the contents thereof which are incorporated by reference in their entirety.

TECHNICAL FIELD

The present application concerns pharmaceutical compositions or formulations of growth hormone compounds.

SEQUENCE LISTING

The instant application contains a Sequence Listing which has been submitted in ASCII format via EFS-Web and is hereby incorporated by reference in its entirety. Said ASCII copy, created on Sep. 22, 2015, is named 8653US02_SeqList.txt and is 3 kilobytes in size.

BACKGROUND

Growth hormone (GH) is a polypeptide hormone secreted by the anterior pituitary in mammals. Dependent on species GH is a protein composed of approximately 190 amino acid residues corresponding to a molecular weight of approximately 22 kDa. GH binds to and signals through cell surface receptors, the GH receptors (GHR). GH plays a key role in promoting growth, maintaining normal body composition, anabolism and lipid metabolism. It also has direct effects on intermediate metabolism, such as decreased glucose uptake, increased lipolysis, and increased amino acid uptake and protein synthesis. The hormone also exerts effects on other tissues including adipose tissue, liver, intestine, kidney, skeleton, connective tissue and muscle.

GH is classified as a four-helix bundle protein exhibiting an "up-up-down-down" topology with two conserved disulphide linkages. Specifically, the mature wild-type human GH (hGH identified by SEQ ID NO: 1) is composed of 191 amino acid residues and has four cysteine residues at positions 53, 165, 182 and 189, which stabilizes the three dimensional structure of the protein by forming two intramolecular disulphide bonds connecting C53 with C165 and C182 with C189, respectively.

Recombinant hGH (somatropin) is commercially available as, for ex: Genotropin® (Pfizer), Nutropin® and Protropin® (Genentech), Humatrope® (Eli Lilly), Serostim® (Serono), Norditropin® (Novo Nordisk), Omnitrope® (Sandoz), Nutropin Depot® (Genentech and Alkermes). Additionally, an analogue with an additional methionine residue at the N-terminal end is also marketed as, for ex: Somatonorm® (Pharmacia Upjohn/Pfizer).

Growth hormone is used to treat growth hormone deficiencies, but unfortunately hGH and the recombinant forms described here above have a relative short half-life which means that patients receiving growth hormone treatment typically need daily growth hormone administrations. Furthermore, for growth hormone being a protein, the administration form is injection which represents a daily inconvenience to the patients.

In order to provide a more convenient product sustained release formulation can be sought or as alternatively it is desirable to provide a growth hormone compound with an extended half-life.

hGH has been subject to extensive mutagenesis and various modifications in attempts to produce hGH analogues and conjugates hereof with altered chemical or biological properties including protease stabilized mutants, cysteine mutants, and PEGylated versions of growth hormone as described in such as US 2003/0162949, WO 02/055532 and WO06/048777.

The quest for growth hormone compounds with increased functionality such as an increased half-life is aimed at reducing the amount of compound needed and the frequency of administration of the therapeutic drug.

Although growth hormone compounds with increased half-life are available, and functional in an experimental setting the compounds must be made available to the patients in a formulation that allows safe and convenient use hereof.

SUMMARY

The present invention in an aspect relates to a pharmaceutical composition comprising a growth hormone compound with prolonged half-life, which is suitable for long time storage. The pharmaceutical composition may comprise a growth hormone conjugate, in particular a growth hormone albumin binder conjugate. The chemical nature of such growth hormone conjugates provides a further challenge for the chemist seeking a pharmaceutical composition that fulfils the requirement and wishes from the industry and patients, e.g. a composition that can be easily prepared, handled and stored preferable also at room temperature and which allows easy and less frequent dosing. The present invention relates to a pharmaceutical composition that maintains stability over prolonged periods of stress including shaking and elevated temperature as a measurement of the stability of the composition.

In one embodiment the pharmaceutical composition according to the invention comprises a growth hormone albumin-binder conjugate, a buffer, a preservative and 0.5-5.0 mg/mL surfactant, such as 1.0-3.0 mg/mL surfactant. The surfactant may be selected from poloxamer 188 and polysorbate 80. The pharmaceutical composition may further comprise a buffer such as histidine to ensure a pH of 6.5-7.0, preferably 6.8. In further embodiments the composition comprises a preservative such as phenol and/or an isotonic agent, such as mannitol.

The growth hormone compound may be a growth hormone albumin-binder conjugate which includes and albumin binding side chain (AB) and a growth hormone protein (GH) that are covalently bound (—) to each other, as represented by the formula AB-GH.

Examples of such conjugates include molecules, wherein AB- is attached to GH via a cysteine residue in GH. The conjugate of the composition may be described with the following formula: A-W—B-Q-GH, wherein GH represents a growth hormone protein or variant, A is an albumin binding residue, B is a (hydrophilic) spacer, Q is a chemical group linking GH and B, W is a chemical group linking B and A and "—" is a covalent bond.

The concentration of the conjugate may be such as 2-15 mg/mL and the composition may be for subcutaneous administration such as once a week e.g. the composition may be for use in a method of treatment by subcutaneous administration once a week.

The composition of the invention is for use in a method of treatment of growth hormone deficiencies or a disease or disorder where the patient will benefit from an increased level of circulating growth hormone.

In further aspects the invention relates to a method of preparation of the pharmaceutical composition according to the invention, the preparation of a pharmaceutical composition for use in methods of treatment, and in particular for use in methods of treatment of growth hormone deficiencies.

The invention further relates to the use of a growth hormone compound for the manufacture of a pharmaceutical composition according to the invention.

In an aspect the invention relates to a method of treatment comprising administering said pharmaceutical composition, for treatment of growth hormone deficiencies or a disease or disorder where the patient benefits from an increased level of circulating growth hormone activity.

SEQUENCE LIST

SEQ ID NO: 1: mature hGH 1-191 (Somatotropin) (referred herein to as hGH for short)
FPTIPLSRLFDNAMLRAHRLHQLAFDTYQEFEEAYIPKEQKYSFLQNPQT
SLCFSESIPTPSNREETQQKSNLELLRISLLLIQSWLEPVQFLRSVFANS
LVYGASDSNVYDLLKDLEEGIQTLMGRLEDGSPRTGQIFKQTYSKFDTNS
HNDDALLKNYGLLYCFRKDMDKVETFLRIVQCRSVEGSCGF

DESCRIPTION

Figure 1:
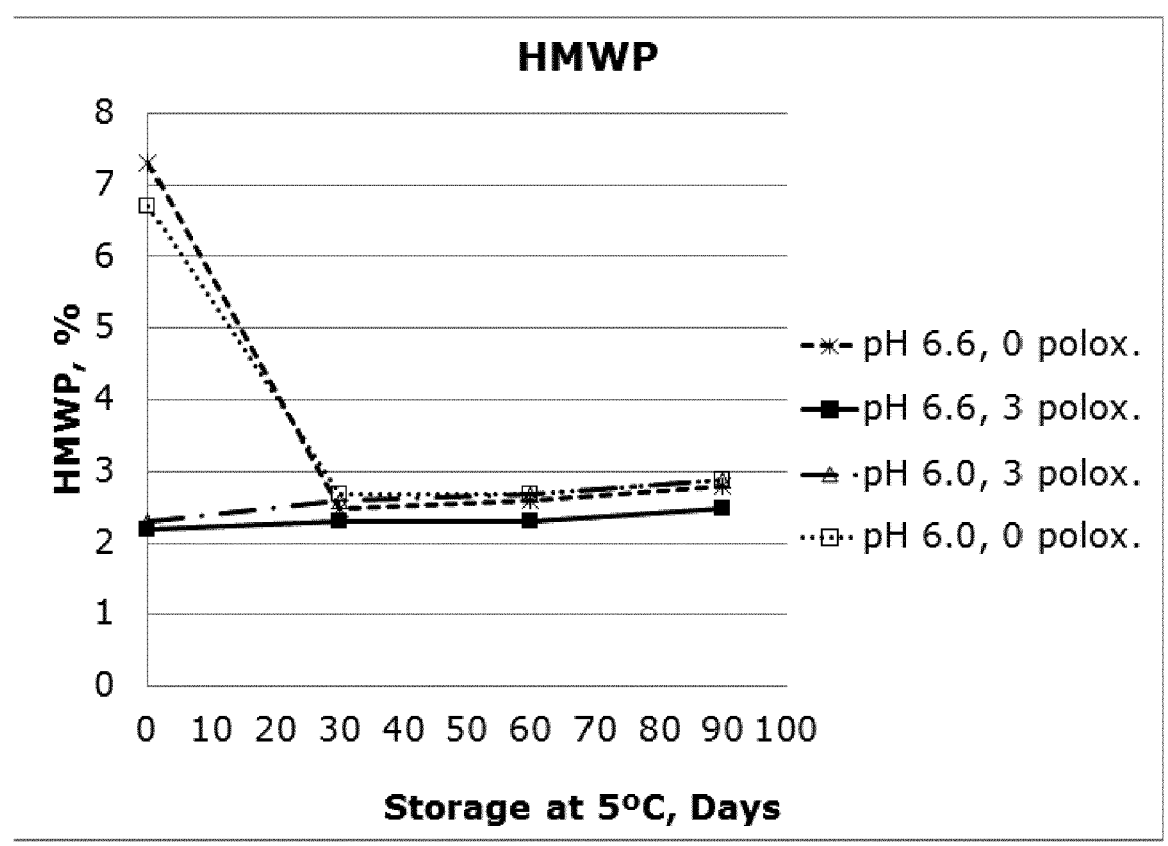
FIG. 1 shows the HMWP content in pharmaceutical compositions comprising 0.0 or 3 mg/mL poloxamer 188 during a storage period of 90 days at 5° C. in buffers with different pH's.

The present application relates to pharmaceutical compositions of growth hormone compounds. The composition or formulation according to the invention should be able to accommodate the growth hormone compound both during production and during storage of the formulation without causing substantial loss of activity, modification or in other ways negatively influence of the growth hormone compound.

An aspect of the present invention relates to a pharmaceutical composition comprising a growth hormone albumin-binder conjugate.

The pharmaceutical composition may be prepared as a liquid composition, wherein liquid compositions may be such as a solution, a suspension or an emulsion.

In further embodiments such compositions are aqueous compositions comprising at least 50% w/w water, such as 50-80% w/w, such as 50-70% w/w, such as 50-60% w/w water.

Growth Hormone Albumin-Binder Conjugate

In order to accommodate the less frequent administration of a growth hormone albumin binder conjugate relative to recombinant hGH, the conjugated must be formulated in a sufficiently high concentration. Concentration of the conjugate may be described in mg/mL or in molar concentrations whereof the latter may be considered more accurate due to the variation in the molecular weight dependent on the albumin binder side chain.

In one embodiment the pharmaceutical composition according to the invention comprises a growth hormone albumin-binder conjugate in a concentration from 2.0 mg/mL to 20.0 mg/mL, such as 3.0-10.0 mg/mL. Depending on the dosage required it may be advantageous to be able to store pharmaceutical compositions with various concentrations of the active ingredient e.g. the growth hormone albumin binder conjugate. In one embodiment the concentration is, such as 6.0-8.0 mg/mL or such as 6.0-7.0 mg/mL. In one embodiment the concentration of the growth hormone albumin-binder conjugate is 6.7 mg/mL. In alternative embodiments the concentration of the growth hormone albumin binder conjugate is 2-5 mg/mL, such as 2.5-4 mg/mL. In a further alternative the concentration of the growth hormone albumin binder conjugate is 8-12 mg/mL, such as 9-11 mg/mL. In a preferred embodiment the composition and concentration of the further components of the pharmaceutical composition remains unchanged while only the concentration of the growth hormone albumin binder conjugate is adjusted.

The growth hormone albumin-binder conjugate is obtained by conjugating an albumin binding side chain to a growth hormone protein. The growth hormone albumin-binder conjugate may thus comprise an albumin binding side chain (AB) and a growth hormone protein (GH) that are covalently bond (—) to each other, as represented by the formula AB-GH. The albumin binding side chain (AB) may be composed of an albumin binding residue (A) and optionally a spacer (B) linked together by a chemical entity (W). The linkage to growth hormone may be via a chemical group Q. The growth hormone albumin-binder conjugate may thus be described by the extended formula: GH-Q-B—W-A. In one embodiment the composition according to the invention comprises a growth hormone albumin-binder conjugate of the formula: GH-Q-B—W-A.

For any growth hormone compound which include either mutations or modifications it is important to consider if those changes affect the activity compared to wt growth hormone. Multiple tests are available to the skilled person and for the purpose of the present application growth hormone compounds, proteins or conjugates are all considered to be biologically active, such as capable of stimulating the growth hormone receptor which may be measured in an BAF assay or in mouse or rat studies know in the art and described in such as WO2011/089255. It is noted that the activity in some assays may be decreased compared to wild type growth hormone, but the increased half-life due the structural changes to the molecule, may counter act this, resulting in a molecule with a prolong effect.

Human growth hormone (hGH) is herein used to described the sequence of the mature human growth hormone protein of 191 amino acid residues as defined by SEQ ID NO: 1.

Although mutations in the sequence of human growth hormone is tolerated a minimal number of mutations is preferred which may be expressed as the level of identity to SEQ ID NO:1. In one embodiment GH of the conjugate is at least 95% identical to hGH, such as 96%, such as 97%, such as 98% or such as 99% identical to hGH.

In further embodiments GH of the conjugates has at most 4 point mutation, such as at most 3 point mutations compared to hGH, such as at most 2 point mutations or such as exactly 1 point mutation compared to hGH.

Linkage of the albumin binding side chain to the GH may be via a wild type residue or a mutant amino acid residue.

In one embodiment the growth hormone (GH) comprises a point mutation in any one of amino acid AA 98-105 compared to human growth hormone. In one embodiment the growth hormone (GH) comprises a Cys mutation, which is substitution of a wt residue for a cysteine in the GH sequence. In one embodiment the GH comprises a Cys mutation in any one of amino acid AA 98-105 compared to human growth hormone.

In one embodiment the growth hormone (GH) includes the L101C mutation.

In one embodiment the side chain (AB) is attached to growth hormone via an amino acid residue in loop 2 (L2, AA99-106) or corresponding residues in a growth hormone variant.

In one embodiment the composition according to invention comprises a growth hormone albumin binder conjugate having the following formula: A-W—B-Q-GH, wherein
GH represents a growth hormone polypeptide,
A is an albumin binding residue,
B is a (hydrophilic) spacer,
W is a chemical group linking A and B,
Q is a chemical group —NH—C(O)—(CH$_2$)— linking GH and B
and "—" is a covalent bond.

In one such embodiment A-W—B-Q- is attached to GH via a Cys residue in GH, which may be such as to a Cys mutation introducing an additional Cys residue.

In one embodiment A-W—B-Q- is attached to L101C of GH.

In a further embodiment A is selected from:

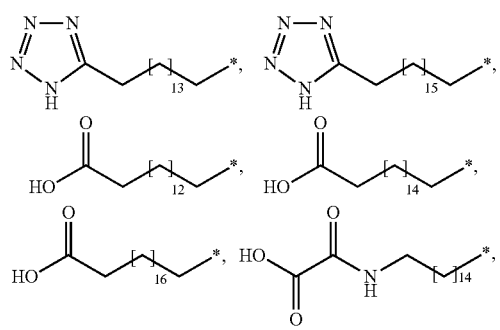

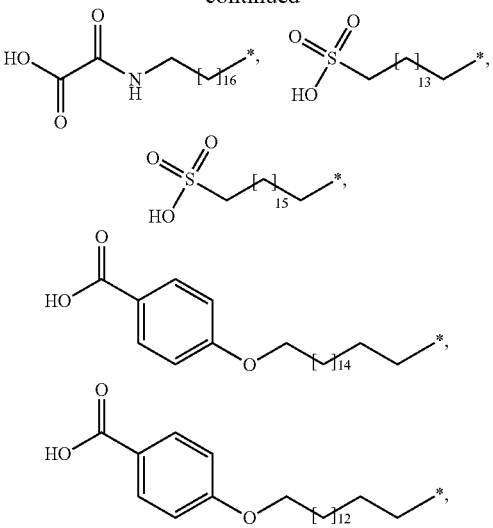

wherein * denotes the attachment to B through W.

In a further embodiment W has the formula: $W_a$-$W_b$, wherein $W_a$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH═CH—, —CH═CHC(O)—, —(CH$_2$)—, —C(O)—, —C(O)O—, —OC(O)—, and $W_b$ is selected from —CH$_2$—C$_6$H$_{12}$—C(═O)—, OEG-, -Lys, -Glu, -γ-Glu-, —CH—, —CH—(CH$_2$—SO$_3$H)—C(O)—, —S(O)$_2$—(CH$_2$)$_3$—C(O)—, or a valence bond.

In a further embodiments W is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH═CH—, —CH═CHC(O)—, —(CH$_2$)—, —C(O)—, —C(O)O—, —OC(O)—, or a valence bond. In a further embodiments W is —C(O)NH—S(O)$_2$—(CH$_2$)$_3$—C(O)—.

In one embodiment the, the spacer B, is a hydrophilic spacer B. The hydrophilic nature of B increases the solubility in water of the albumin binding side chain (AB- or A-W—B-Q-) and the resulting growth hormone conjugate. Therefor such side chains and compounds are well suited for aqueous solutions both during processing and for storage. At least part of the compound will thus have a tendency to interact with water molecules and thus dissolve in water and other polar substances or solvents.

In one embodiment the, the spacer B comprises at least one OEG motif, the radical 8-amino-3,6-dioxaoctanic acid, i.e. —NH—(CH$_2$)$_2$—O—(CH$_2$)$_2$—O—CH$_2$—C(O)—.

In a further specified embodiment the hydrophilic spacer (B) comprise at least two OEG motifs. The orientation of such OEG motif(s) is in one embodiment so that the —C(O)— is closest to the growth hormone compound, while —NH— is closest to the albumin binding residue.

In additional embodiments comprising two OEG motifs the two motifs have identical orientation or different orientation. In an embodiment two such OEG motifs are located beside each other, whereas in alternative embodiments such OEG motifs are separated by one or more covalently linked atoms.

In an embodiment the hydrophilic spacer comprise at least one glutamic acid residue. The amino acid glutamic acid comprises two carboxylic acid groups. Its gamma-carboxy group may be used for forming an amide bond with the epsilon-amino group of lysine, or with an amino group of an OEG molecule, if present, or with the amino group of another Glu residue, if present. The alfa-carboxy group may alternatively be used for forming a similar amide bond with the epsilon-amino group of lysine, or with an amino group of an OEG molecule, if present, or with the amino group of another Glu residue, if present. The amino group of Glu may in turn form an amide bond with the carboxy group of the albumin binding residue, or with the carboxy group of an OEG motif, if present, or with the gamma-carboxy group or alfa carboxy group of another Glu, if present. The linkage of the amino group of one Glu to a gamma-carboxy group of a second Glu may be referred to as a "gamma-Glu" motif.

In an embodiment the hydrophilic spacer comprise at least one combined OEG-Glu motif (—NH—$(CH_2)_2$—O—$(CH_2)_2$—O—$CH_2$—C(O)NH—CH(C(O)OH)—$(CH_2)_2$—C(O)—) or at least one combined Glu-OEG motif (—NH—CH(C(O)OH)—$(CH_2)_2$—C(O)NH—$(CH_2)_2$—O—$(CH_2)_2$—O—$CH_2$—C(O)—) or combinations here of, wherein such Glu-OEG and OEG-Glu motifs may be separated by one or more covalently linked atoms or directly bond to each other by an amide bond of the Glu's forming a gamma-Glu.

In an embodiment the hydrophilic spacer comprise at least one combined OEG-Lys motif (—NH—$(CH_2)_2$—O—$(CH_2)_2$—O—$CH_2$—C(O)NH—CH(C(O)OH)—$(CH_2)_4$—NH—) or at least one combined Lys-OEG motif (—NH—CH(C(O)OH)—$(CH_2)_4$—NHC(O)—$CH_2$—O—$(CH_2)_2$—O—$(CH_2)_2$—NH—) or combinations here of, where in such Lys-OEG and OEG-Lys motifs may be separated by one or more covalently linked atoms.

In a further embodiment B has the formula; —$X_1$—$X_2$—$X_3$—,
wherein
$X_1$, $X_2$ and $X_3$ independently are selected from a valance bond and the elements of OEG-, -Lys-, -Glu- and -γ-Glu- which may all be linked though peptide bonds, where $X_3$ is preferably an OEG- or Lys-.

In an embodiment B has the formula; —$X_1$—$X_2$—$X_3$—$X_4$—,
wherein
$X_4$ is NH—CH(—COOH)—$(CH_2)_4$NH—,
$X_3$ is -OEG-,
$X_2$ is -γ-Glu-γ-Glu- and
$X_1$ is -OEG-.

In an embodiment B has the formula; —$X_1$—$X_2$—$X_3$—$X_4$—,
wherein
$X_4$ is —NH—CH(—COOH)—$(CH_2)_4$NH—,
$X_3$ is -OEG-,
$X_2$ is -γ-Glu-γ-Glu- and
$X_1$ is a valence bond.

In an embodiment B has the formula; —$X_1$—$X_2$—$X_3$—,
wherein
$X_1$ is —$W_1$—$[(CHR^1)_{l1}$—$W_2]_{m1}$—$\{[(CH_2)_{n1}E1]_{m2}$—$[(CHR^2)_{l2}$—$W_3]_{m3}\}_{n2}$,
$X_2$ is —$[(CHR^3)_{l3}$—$W_4]_{m4}$—$\{[(CH_2)_{n3}E2]_{m5}$—$[(CHR^4)_{l4}$—$W_5]_{m6}\}_{n4}$—,
$X_3$ is —$[(CHR^5)_{l5}$—$W_6]_{m7}$—,
l1, l2, l3, l4 and l5 independently are selected from 0-16,
m1, m3, m4, m6 and m7 independently are selected from 0-10,
m2 and m5 independently are selected from 0-16,
n1, n2, n3 and n4 independently are selected from 0-6,
$R^1$, $R^2$, $R^3$, $R^4$ and $R^5$ independently are selected from hydrogen, —C(O)OH, —C(O)$NH_2$, —S(O)OH, —S(O)$_2$OH, —$CH_2$S(O)$_2$OH, —NH—C(=NH)—$NH_2$ or $C_{1-6}$-alkyl; wherein the alkyl groups optionally are substituted with —C(O)OH, —C(O)$NH_2$, —S(O)OH, —S(O)$_2$OH, —CN or —OH,
E1 and E2 independently are selected from —O—, —N($R^6$)—, —N(C(O)$R^7$)— or a valence bond; wherein $R^6$ and $R^7$ independently represent hydrogen or $C_{1-6}$-alkyl,
$W_1$ to $W_6$ independently are selected from —C(O)NH—, —NHC(O)—, —$(CH_2)_{s1}$C(O)NH—, —C(O)NHCH$_2$—, —$CH_2$NHC(O)—, —C(O)NHS(O)$_2$—, —S(O)$_2$NHC(O)—, —OC(O)NH—, —NHC(O)O—, —C(O)$CH_2$—, —$CH_2$C(O)—, —C(O)CH=CH—, —CH=CHC(O)—, —$(CH_2)_{s2}$—, —C(O)—, —C(O)O—, —OC(O)—, or a valence bond; wherein s1 and s2 independently are 0, 1, 2, 3 or 4.

In a further embodiment l1, l2, l3, l4 and l5 independently are 0-6. In a further embodiment m1, m3, m4, m6 and m7 independently are 0-6. In a further embodiment m2 and m5 independently are 0-10. In a further embodiment n1, n2, n3 and n4 independently are 0-4. In a further embodiment E1 and E2 are independently selected from —O— or —N($R^6$)— or a valence bond.

In a further embodiment $W_1$ through $W_6$ independently are selected from the group consisting of —C(O)NH—, —NHC(O)—, —$CH_2$NHC(O)—, —$(CH_2)_{s1}$C(O)NH—, —C(O)NHS(O)$_2$—, —S(O)$_2$NHC(O)—, —NHC(O)$C_{1-6}$-alkyl, —C(O)NH$C_{1-6}$-alkyl or a valence bond; wherein the alkyl group is optionally substituted with oxo.

In a further embodiment $R^1$, $R^2$, $R^3$, $R^4$ and $R^5$ independently are selected from hydrogen, —C(O)OH, —C(O)$NH_2$, —S(O)$_2$OH or $C_{1-6}$-alkyl; wherein the $C_{1-6}$-alkyl group optionally is substituted with —C(O)OH, —C(O)$NH_2$ or —S(O)$_2$OH.

In a further embodiment —$\{[(CH_2)_{n1}E1]_{m2}$—$[(CHR^2)_{l2}$—$W_3]_{m3}\}_{n2}$— and —$\{[(CH_2)_{n3}E2]_{m5}$—$[(CHR^4)_{l4}$—$W_5]_{m6}\}_{n4}$—, wherein E1 and E2 are —O—, are selected from

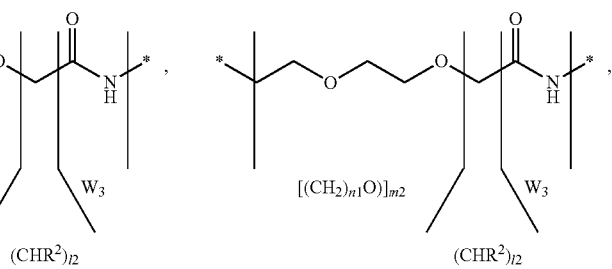

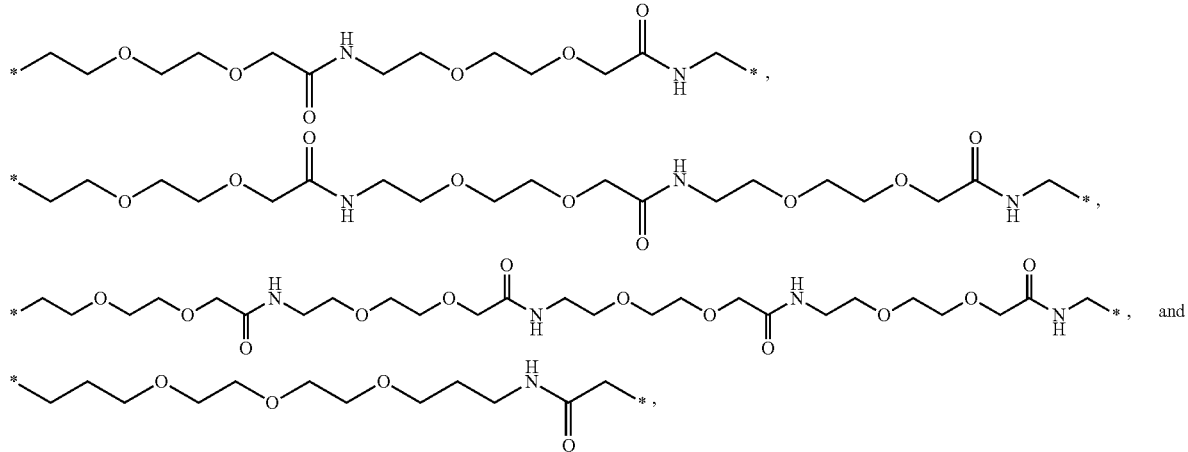
wherein * is intended to denote a point of attachment, ie, an open bond.
In a further embodiment B is selected from:
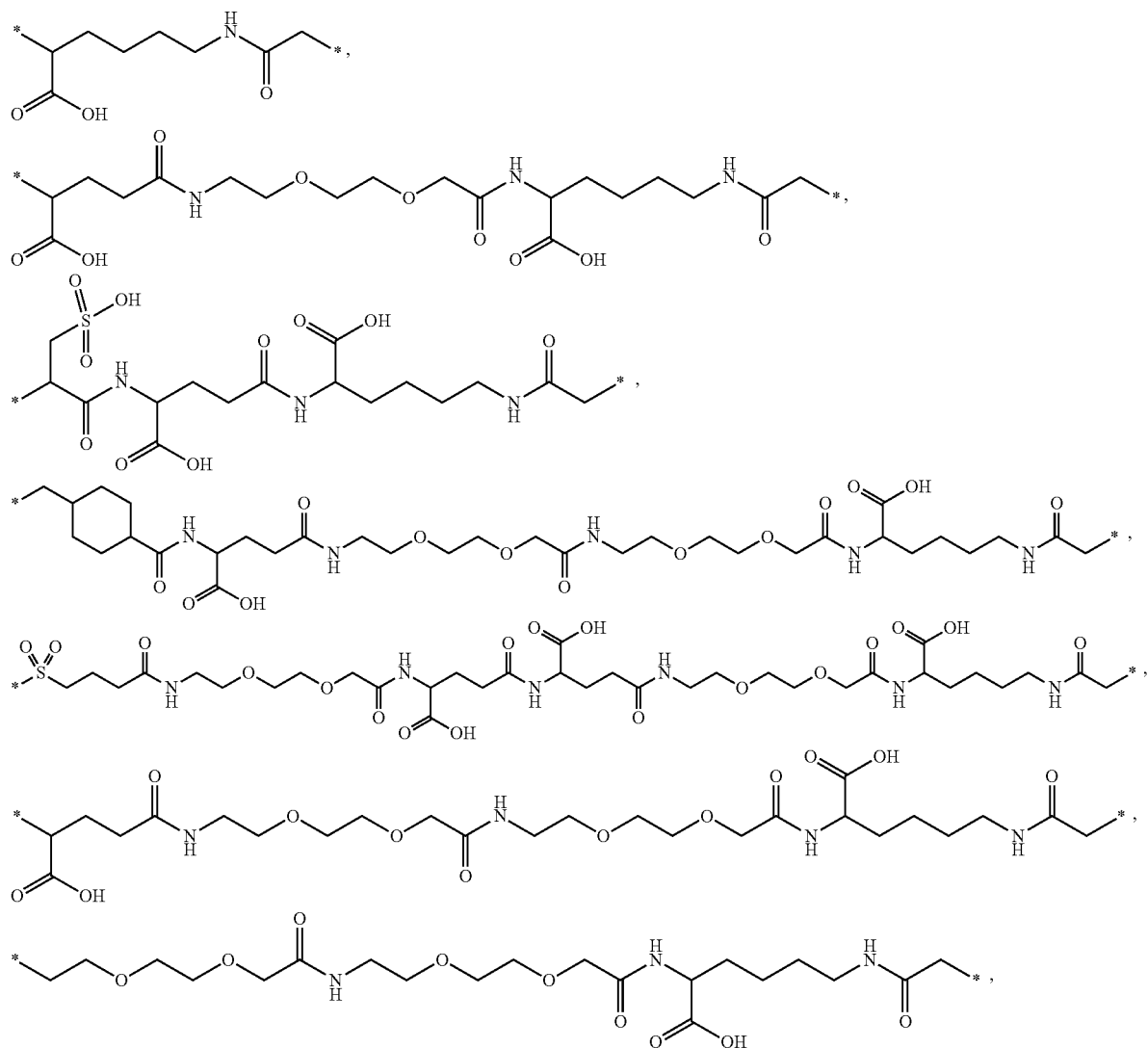

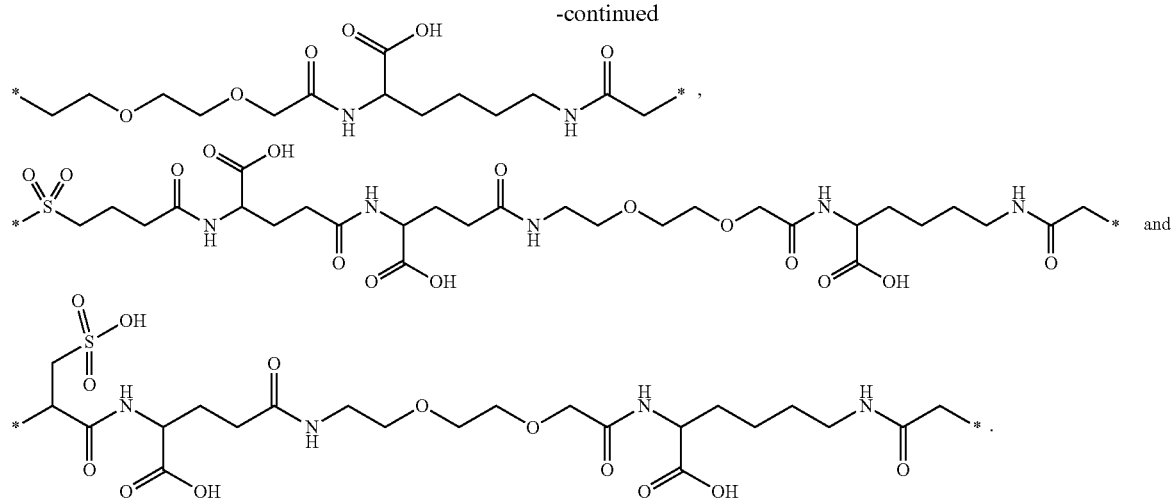
In a further embodiment the GH conjugate is selected from:
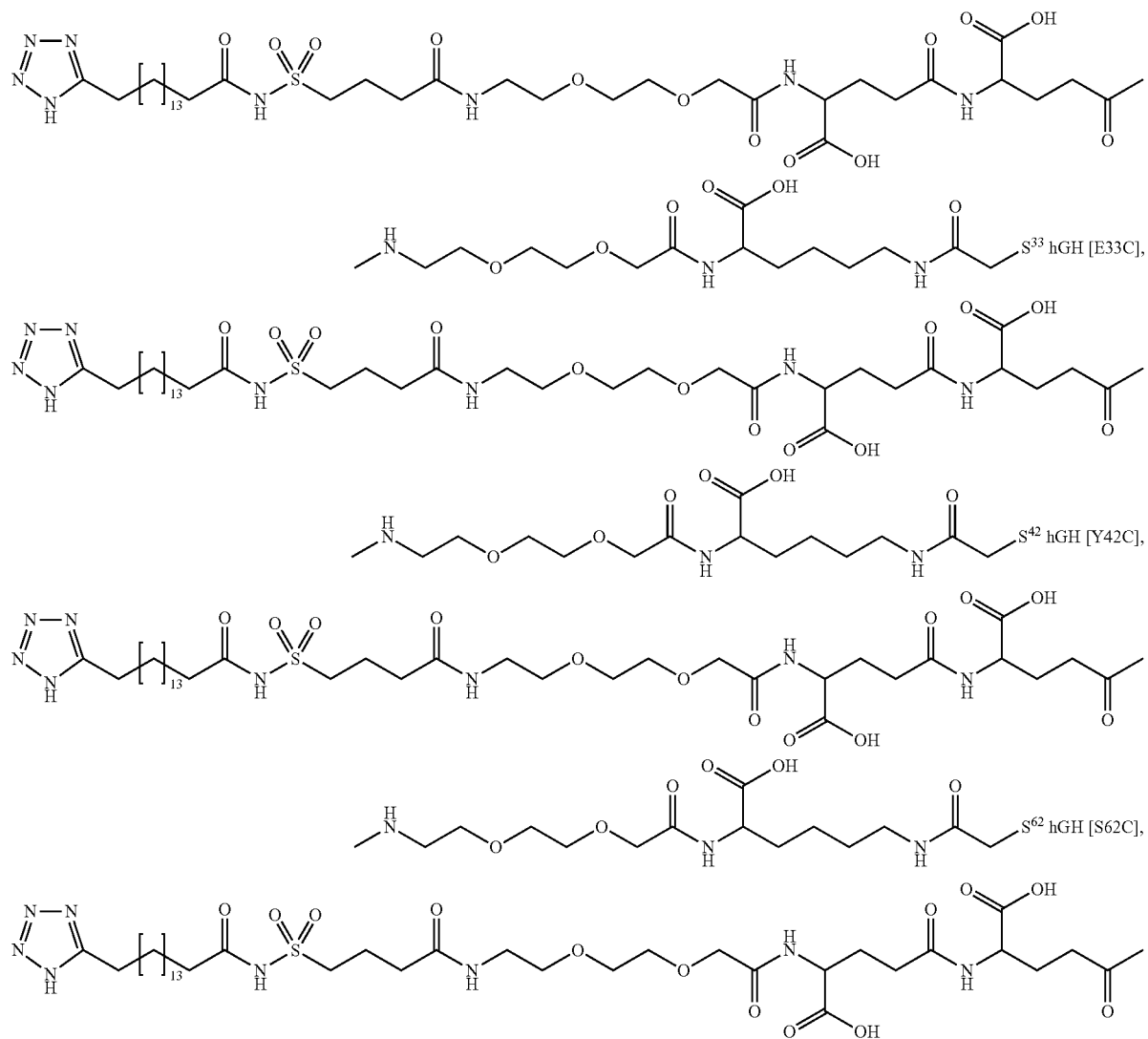

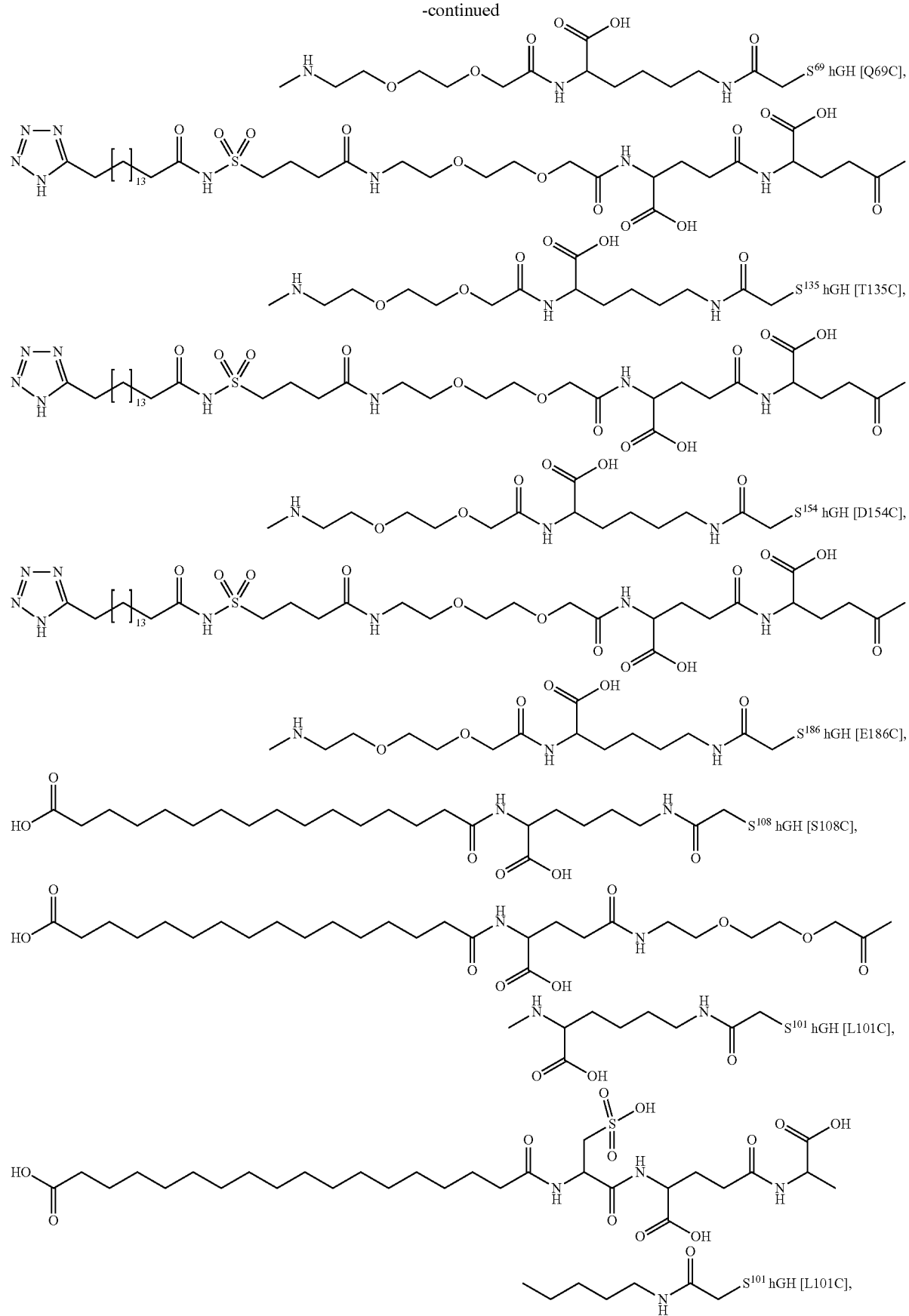

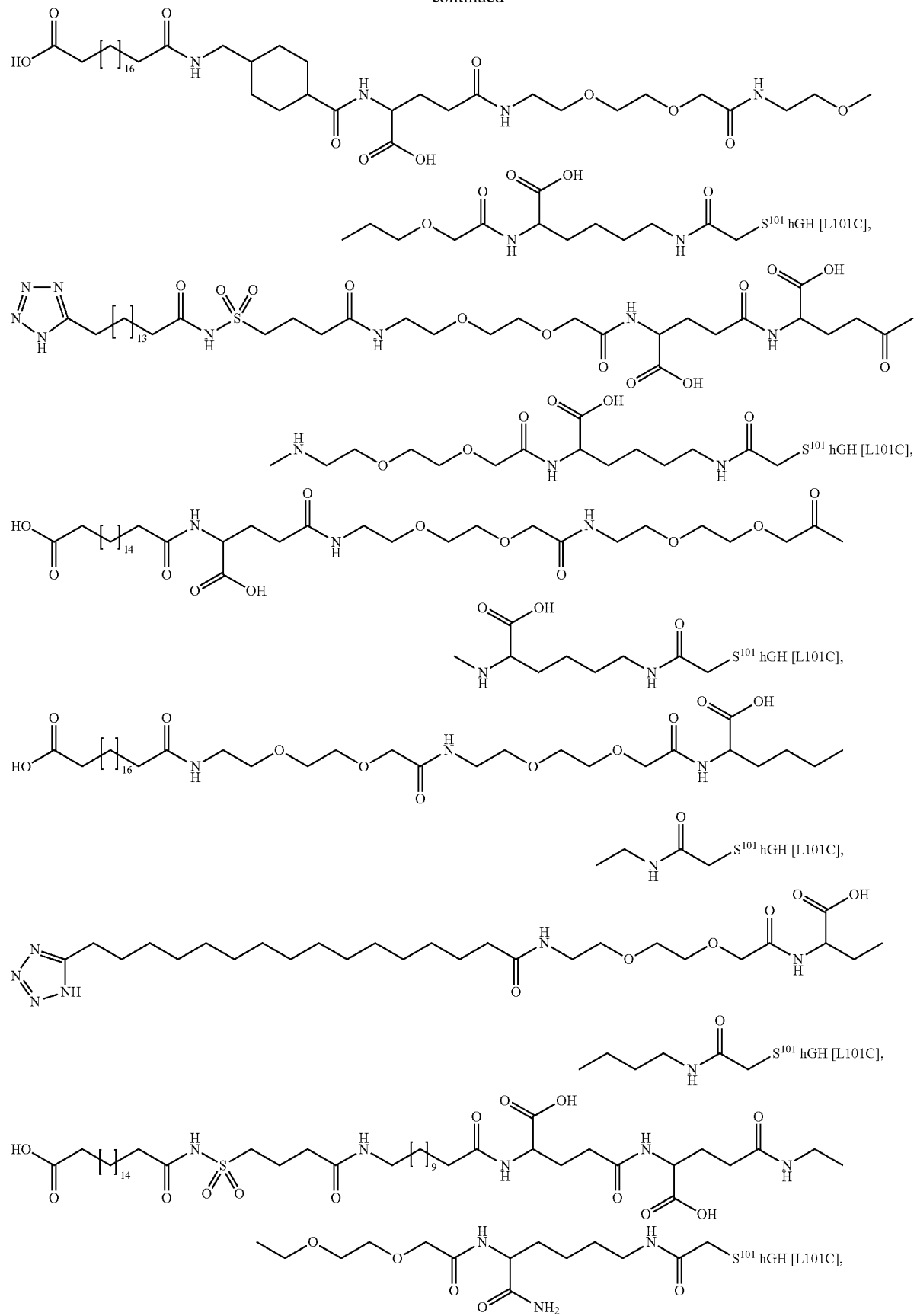

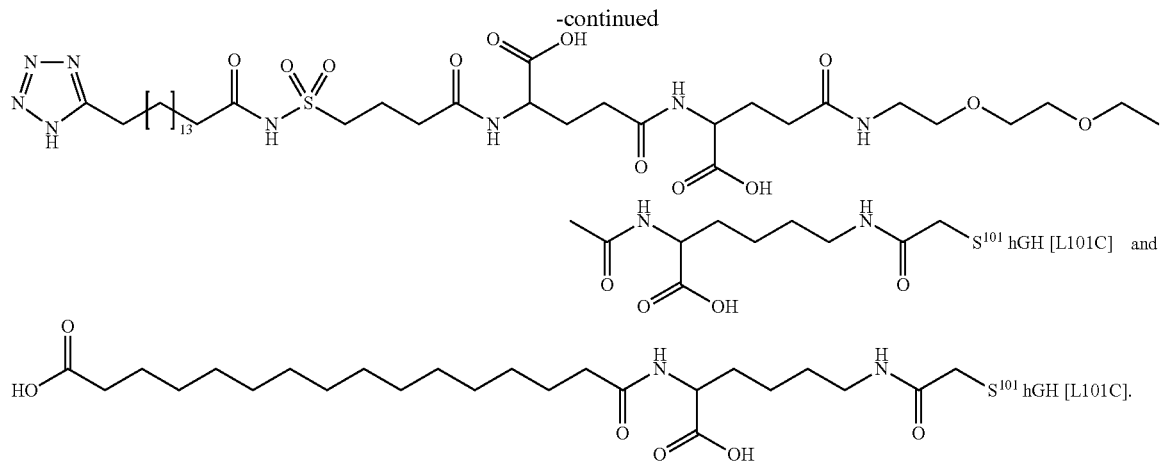

Pharmaceutical Excipients

As described herein above the present invention concerns a pharmaceutical composition comprising a growth hormone conjugate and a surfactant capable of stabilizing the formulation.

The composition may further comprise pharmaceutical excipients, such as a buffer system, preservative(s), tonicity agent(s), chelating agent(s), stabilizers and further surfactants. For convenience reference is made to Remington: *The Science and Practice of Pharmacy*, 20$^{th}$ edition, 2000.

In one embodiment of the invention the pharmaceutical composition is a liquid formulation. In one embodiment of the invention the pharmaceutical composition is an aqueous composition, i.e. a composition where the components are dissolved or suspended in water. Such composition is typically a solution or a suspension. If the composition comprises components which cannot be dissolved in water the composition may be an emulsion of two liquids, frequently water and an oil or a fatty acid based liquid. In another embodiment the pharmaceutical composition is a freeze-dried composition, whereto the physician or the patient adds solvents and/or diluents prior to use.

It is well known that human growth hormone is an unstable protein that reacts to pH changes by both deamination and aggregation. It is thus of high interest to determine for new growth hormone compound which pH and buffer composition that provides high stability, In one embodiment the composition of the invention has a pH of 5.0-8.0, such as from 6.0-7.5, such as from 6.5-7.0. The pH may also be 6.6-6.9 or 6.7-6.9. In further embodiments the pH of the composition is 6.6, 6.7, 6.8, 6.9 or 7.0.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. In one embodiment the pharmaceutical composition does not include glycine. In one embodiment composition comprises histidine as buffer.

In one embodiment the composition comprises histidine and has a pH of 6.5-7.0.

In one embodiment the concentration of histidine is from 0.5 mg/mL to 2 mg/mL, such as from 0.6-1.0 mg/mL, such as from 0.6-0.8 mg/mL, or from 0.6-0.7 mg/mL, such as 0.65-0.70 mg/mL or around 0.7 mg/mL. In an alternative embodiment the concentration of histidine is from 1.0-2.0 mg/mL, or such as from 1.5-1.8 mg/mL, or such as from 1.5-1.6 mg/mL, such as around 1.5 mg/mL.

Growth hormone and in particular growth hormone conjugates display an undesirable tendency to aggregate. In the present case the hydrophobic albumin binder linked to growth hormone may create an increased tendency for aggregation of the molecule when diluted in a pharmaceutical composition.

A surfactant may help to increase the water solubility of hydrophobic, oily substances or otherwise increase the miscibility of two substances with different hydrophobicity's and hence opposite solubility. A surfactant may further help to decrease aggregation by interaction between the surfactant and the protein molecule in a liquid pharmaceutical composition. In an embodiment of the invention the composition comprises a surfactant.

In a further embodiment of the invention the surfactant is a polyoxypropylene-polyoxyethylene block polymer. In one embodiment the surfactant is selected from non-ionic surfactants, such as poloxamers including Pluronic® F68, poloxamer 188 and 407 and Triton X-100. In one embodiment the surfactant is selected from polyoxyethylene and polyethylene derivatives such as alkylated and alkoxylated derivatives (tweens, e.g. Tween-20, Tween-40, Tween-80 and Brij-35). In one embodiment the surfactant is polysorbate 80. In one embodiment the composition of the invention comprises a surfactant selected from poloxamer 188 and polysorbate 80). In one embodiment the surfactant is poloxamer 188

In one embodiment the composition comprises 0.1-5.0 mg/mL surfactant, such as. 0.5-3.0 mg/mL surfactant, such as poloxamer 188 or polysorbate 80.

In one embodiment the composition comprises 1 mg/mL poloxamer 188.

In one embodiment the composition comprises histidine and has a pH of 6.5-7.0 and includes a surfactant. In one embodiment the composition comprises histidine and has a pH of 6.5-7.0 and comprises 0.1-5.0 mg/mL poloxamer 188, such as 1.0.-3.0 mg/mL poloxamer 188, or 3 mg/mL.

In a further embodiment of the invention the composition further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3-(p-chlorphenoxy)propane-1,2-diol) or mixtures thereof.

In one embodiment the composition comprises phenol.

In a further embodiment of the invention the preservative is present in a concentration from 0.1 mg/mL to 20 mg/mL. In a further embodiment of the invention the preservative is present in a concentration from 0.1 mg/mL to 5 mg/mL. In one embodiment the composition according to the invention comprises 2.0-4.0 mg/mL phenol, such as 3.0-4.0 mg/mL phenol.

Method for Preparing a Pharmaceutical Composition

As a starting point for preparation of a pharmaceutical composition the Growth hormone albumin-binder conjugate is provided in a solution, usually an aqueous solution. This starting solution is preferably highly concentrated to allow dilution during preparation of the pharmaceutical compositions. In one embodiment the starting solution of the growth hormone albumin-binder conjugate is more than 15 mg/mL, such as 15-30 mg/mL, or such as 15-25 mg/mL.

The usual method of preparation is to dissolve the excipients (buffer, surfactant, isotonic agent and preservative in water) in a 2× buffer solution which includes each excipient in the double concentration of the concentration of the final compositions.

Depending on the concentration of the growth hormone albumin-binder conjugate solution (starting solution) an appropriate volume of this is added to include the amount required to reach the concentration of the final pharmaceutical compositions. The mixing may be performed by slowly adding the compound solution and ensuring continuous mixing by stirring. Finally, water is added to reach the total volume. The pH may be adjusted at different steps, such as one or more of the compound solution, the 2× buffer and the final pharmaceutical composition.

The skilled person will know how to modify the methods in various ways such as to adjust concentrations of the 2× buffer if a different mixing relationship is required or if one or more of the components of the final composition is already present in the compound solution, wherefore the concentration of such components in the 2× buffer should be less than the double of the end concentration.

Example 8 and 9 herein describes preparation of GH compositions with adjustments to the above general method. A key information is the need to avoid mixing GH with high concentration of phenol.

Methods of Treatment

As described in the background section growth hormone products are suitable for treatment of growth hormone deficiencies. Basically a pharmaceutical composition according to the invention may be for use in treatment of any disease or disorder where the patient will benefit from an increase in circulating growth hormone activity. In current treatments a growth hormone protein is administered. As an alternative growth hormone compounds with a prolonged half-life may be administered to provide growth hormone activity.

An aspect of the invention relates to the use of the growth hormone composition for the manufacture of a medicament for treatment, in particular treatment of growth hormone deficiency in children and/or adults or other diseases or states where the patient benefit from an increased level of growth hormone as described herein.

The invention further relates to the aspects of preparation of a pharmaceutical composition according to the invention for use in a method of treatment as well as the pharmaceutical composition for use in a method of treatment.

In such embodiments, the pharmaceutical composition according to the invention is for use in a method of treatment or prevention of growth hormone deficiency in children and/or adults. Other diseases or disorders where an increased concentration of circulating growth hormone may be helpful may also be treated or prevented using the pharmaceutical composition of the invention. In one embodiment the pharmaceutical compositions of the invention is for use in a method for treating diseases or states where a benefit from an increase in the amount of circulating growth hormone is observed. Such diseases or states include growth hormone deficiency (GHD); Turner Syndrome; Prader-Willi syndrome (PWS); Noonan syndrome; Down syndrome; chronic renal disease, juvenile rheumatoid arthritis; cystic fibrosis, HIV-infection in children receiving HAART treatment (HIV/HALS children); short children born short for gestational age (SGA); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in e.g. hand, knee, or shoulder; patients having or going through distraction oteogenesis; patients after hip or discus replacement, meniscus repair, spinal fusions or prosthesis fixation, such as in the knee, hip, shoulder, elbow, wrist or jaw; patients into which osteosynthesis material, such as nails, screws and plates, have been fixed; patients with non-union or mal-union of fractures; patients after osteatomia, e.g. from tibia or 1st toe; patients after graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Chron's disease; IBD, UC, impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; or short stature due to glucocorticoid treatment in children. Growth hormones have also been used for acceleration of the healing of muscle tissue, nervous tissue or wounds; the acceleration or improvement of blood flow to damaged tissue; or the decrease of infection rate in damaged tissue.

In one embodiment, the growth hormone compound and compositions hereof is for treatment of GHD in children, GHD in adults (AGHD), Turner syndrome (TS), Noonan syndrome, Idiopathic short stature (ISS), Small for gestational age (SGA), Prader-Willi syndrome (PWS), Chronic renal insufficiency (CRI), Skeletal dysplasia, SHOX deficiency, AIDS wasting, HIV associated lipdystrophy (HARS), Short bowel syndrome optionally including, steroid dependent disease, cystic fibrosis and fibromyalgia.

In one embodiment the growth hormone albumin-binder conjugate is for use in the manufacture of a pharmaceutical composition as described herein.

In one embodiment, the present invention relates to a method of treating diseases or states mentioned above, wherein the activity of the pharmaceutical composition according to the invention is useful for treating said diseases or states. The administering of the pharmaceutical composition e.g. the growth hormone albumin-binder conjugate resulting in a therapeutic benefit associated with an increase in the amount of circulating growth hormone compound in the patient. In an embodiment said method comprises, administering to a patient an effective amount of the pharmaceutical composition comprising a growth hormone albumin-binder conjugate thereby ameliorating the symptoms of said patient.

In one embodiment, the present invention relates to a method comprising administration to a patient in need thereof an effective amount of a therapeutically effective amount of a pharmaceutical composition according to the invention. The present invention thus provides a method for treating these diseases or states, the method comprising administering to a patient in need thereof a therapeutically effective amount of a growth hormone albumin-binder conjugate in a pharmaceutical composition according to the present invention.

A "therapeutically effective amount" of a compound of the invention as used herein means an amount sufficient to cure, alleviate or partially arrest the clinical manifestations of a given disease and its complications. An amount adequate to accomplish this is defined as "therapeutically effective amount".

Effective amounts for each purpose will depend on e.g. the severity of the disease or injury as well as the weight, sex, age and general state of the subject.

As described herein the growth hormone albumin-binder conjugate of the pharmaceutical composition have an extended half-life aimed at increasing the exposure in the patient to the compound after each dosage and the administration regime of the pharmaceutical composition should be adjusted to reach an effective exposure.

In one embodiment the pharmaceutical composition is for administration by subcutaneous injections.

In one embodiment the pharmaceutical composition is for use in a method of treatment by subcutaneous injections.

Figure 6:
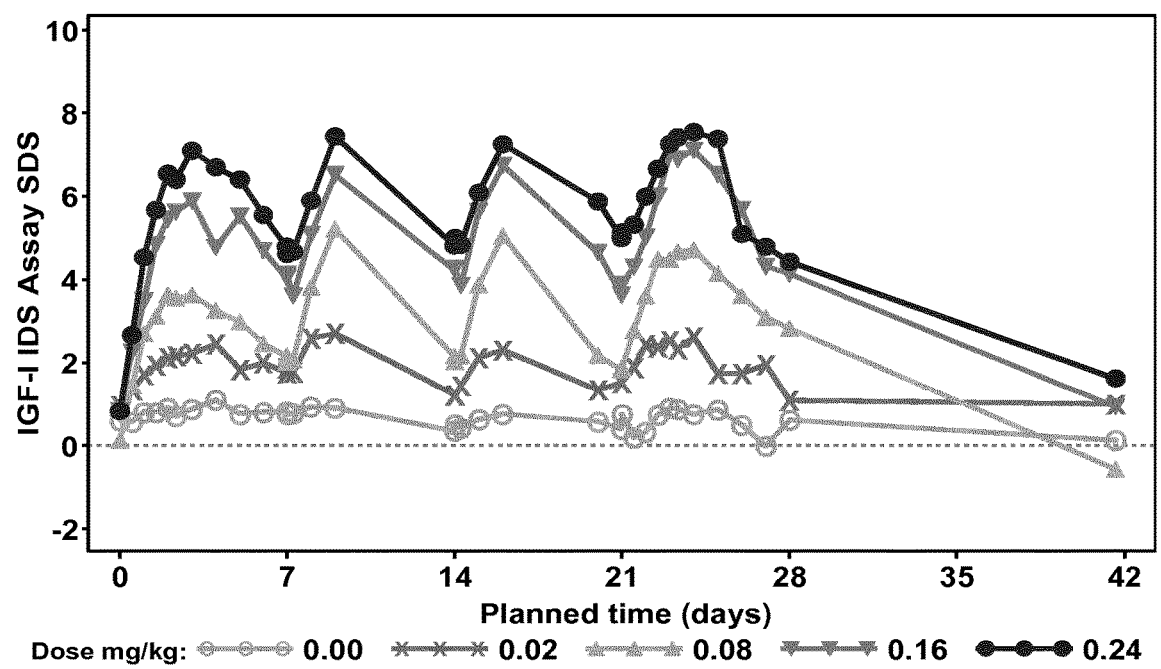
FIG. 6 shows the mean IGF-I standard deviation score in Japanese subjects (A) and non-Asian subjects (B).
Figure 6:
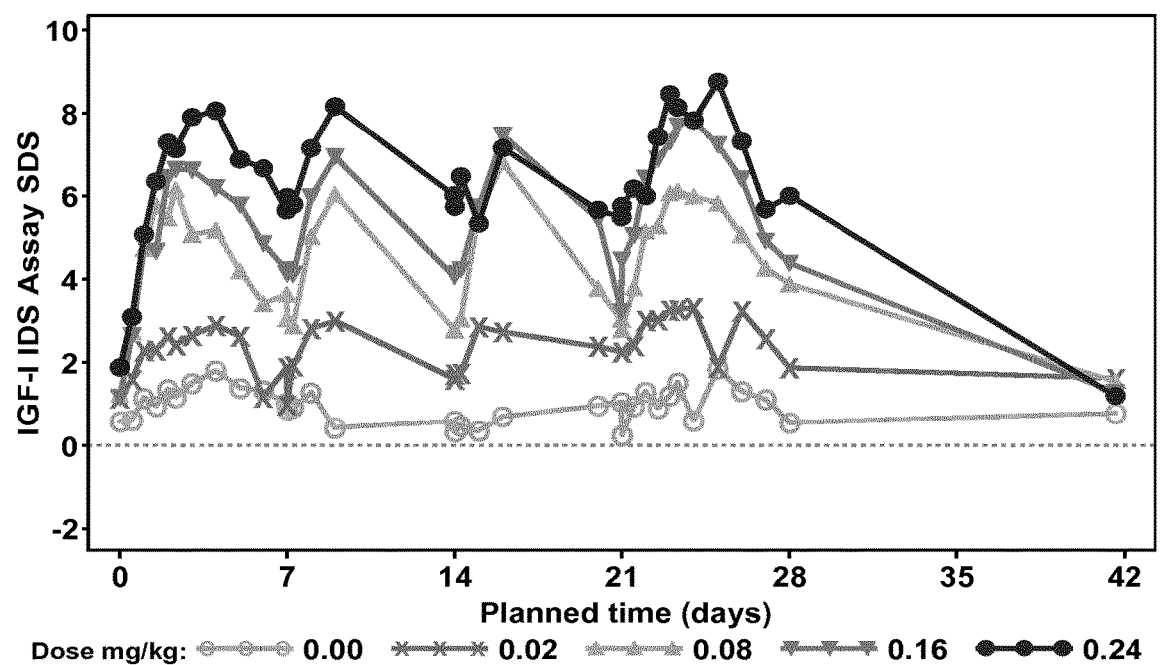

As the IGF-1 response is a hallmark of GH functionality, the therapeutically effective dosage may be estimate based on the IFG-1 response of a given growth hormone albumin-binder conjugate. As seen in FIG. 6, administration of conjugate I result in dose dependent IGF-1 responses with elevated IGF-1 levels at all dosages demonstrating that such compounds are suitable for once weekly administration.

In one embodiment the pharmaceutical composition is for use in a method of treatment administering the growth hormone conjugate in an amount of about 0.01-2.0 mg/kg per dosage. In adults the composition may be for administering 0.02-0.10 mg/kg, or such as 0.02-0.08 mg/kg or such as 0.03-0.06, 0.02-0.05 mg/kg or such 0.02-0.04 mg/kg of the growth hormone conjugate per dosage. In further embodiments the pharmaceutical composition is for use in a method of treatment administering 0.05-0.18 mg/kg such as 0.08-0.16 mg/kg of the growth hormone conjugate per dosage if the subject in need is a child. As is seen the range may be wider for adults and may also dependent of gender, although usually within the range of 0.01-0.08 mg/kg.

Current treatment options are mainly once daily injects with one of several recombinant growth hormone products.

In an embodiment the pharmaceutical composition is for use in a method of treatment by administration about once a week, or every $7^{th}$ day, a or maybe even for administration once every $10^{th}$ day.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention is further described in the following none-limiting embodiments and illustrated by the Examples provided further below.

EMBODIMENTS

1. A pharmaceutical composition comprising
   a) 2-20 mg/mL growth hormone albumin-binder conjugate and
   b) 0.5-5.0 mg/mL surfactant.
2. The composition according to embodiment 1, wherein the composition comprises 0.5-4.0 mg/mL surfactant.
3. The composition according to embodiment 1, wherein the composition comprises 1.0-3.0 mg/mL surfactant.
4. The composition according to embodiment 1, wherein the composition comprises around 1.0 mg/mL surfactant.
5. The composition according to any of embodiments 1-4, wherein the composition comprises a surfactant selected from poloxamer 188 and polysorbate 80.
6. The composition according to embodiment 1, wherein the composition comprises 1 mg/mL poloxamer 188 as surfactant.
7. The composition according to any of the embodiments 1-6, wherein the composition comprises a buffer.
8. The composition according to any of the embodiments 1-6, wherein the composition comprises a buffer selected from the group consisting: of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof.
9. The composition according to any of the embodiments 1-6, wherein the composition comprises a buffer selected from the group consisting of: citrate, glycylglycine, histidine, glycine, lysine and arginine.
10. The composition according to any of the embodiments 1-6, wherein the composition comprises a buffer selected from the group consisting of: sodium dihydrogen phosphate, disodium hydrogen phosphate, sodium phosphate and tris(hydroxymethyl)-aminomethan.
11. The composition according to any of the previous embodiments, wherein the composition does not comprise glycine.
12. The composition according to any of embodiments 1-9, wherein the composition comprises histidine buffer.
13. The composition according to any of embodiments 1-9, wherein the composition comprises histidine buffer in a concentration of 0.5-2 mg/mL.
14. The composition according to any of embodiments 1-13, wherein pH of the composition is 6.0-8.0, such as 5-7.0, or such as around 6.8.
15. The composition according to any of t embodiments 1-14, wherein the composition comprises an isotonic agent.

16. The composition according to any of t embodiments 1-14, wherein the composition comprises an isotonic agent, wherein the isotonic agent is a sugar alcohol.
17. The composition according to any of t embodiments 1-14, wherein the composition comprises an isotonic agent, wherein the isotonic agent is mannitol.
18. The composition according to any of embodiments 1-14, wherein the composition comprises 20-50 mg/mL of an isotonic agent.
19. The composition according to any of embodiments 1-18, wherein the composition comprises 20-50 mg/mL mannitol.
20. The composition according to any of embodiments 1-18, wherein the composition comprises 40-50 mg/mL mannitol.
21. The composition according to any of embodiments 1-18, wherein the composition comprises a preservative.
22. The composition according to any of embodiments 1-18, wherein the composition comprises phenol as preservative.
23. The composition according to any of the previous embodiments, wherein the composition comprises 2.0-4.0 mg/mL phenol, such as 3.0-4.0 mg/mL.
24. The composition according to embodiment 1, wherein the growth hormone albumin-binder conjugate includes and albumin binding side chain (AB) and a growth hormone protein (GH) that are covalently linked (—) to each other, as represented by the formula AB-GH.
25. The composition according to any of the previous embodiments, wherein GH comprises at least one point mutation compared to human growth hormone.
26. The composition according to embodiment 25, wherein the growth hormone comprises one point mutation in any one of amino acid AA 98-105 compared to human growth hormone.
27. The composition according to embodiment 25, wherein the point mutation is a Cys mutation.
28. The composition according to embodiment 25, wherein the growth hormone include the L101C mutation.
29. The composition according to embodiment 24, wherein the side chain (AB) is attached to growth hormone via an amino acid residue in loop 2 (L2, AA99-106) or corresponding residues in a growth hormone variant.
30. The composition according to embodiment 24, wherein AB- is attached to GH via a Cys residue in GH.
31. The composition according to embodiment 24, wherein AB- is attached to L101C of GH.
32. The composition according to any of the previous embodiments, wherein the growth hormone albumin binder conjugate has the following formula:

A-W—B-Q-GH

GH represents a growth hormone protein/compound
A is an albumin binding residue
B is a (hydrophilic) spacer
Q is a chemical group linking GH and B,
W is a chemical group linking B and A.
and "—" is a covalent bond.
33. The composition according to embodiment 32, wherein the wherein A-W—B-Q- is attached to an L101C mutation in GH.
34. The composition according to embodiment 32 or 33, wherein the chemical group Q is: NH—C(O)—(CH$_2$)—.
35. The composition according to embodiment 32 or 33 or 34, wherein A is selected from:

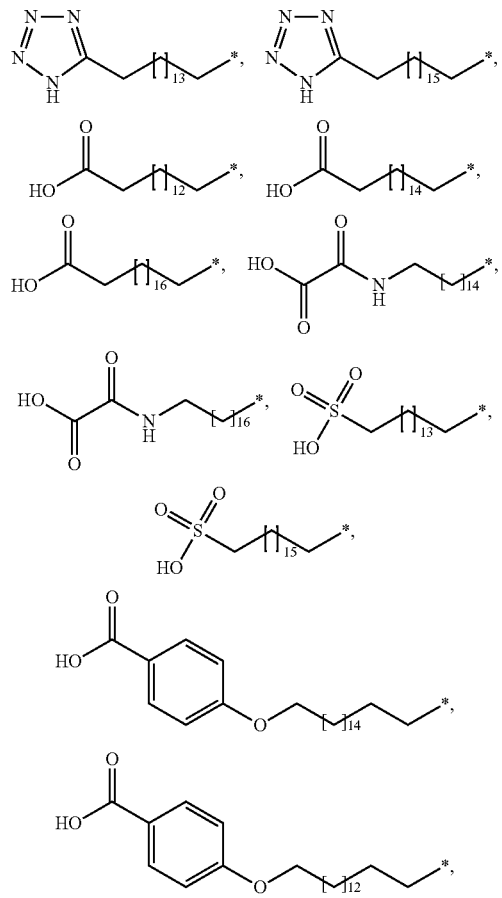

wherein * denotes the attachment to B through W.

36. The composition according to embodiment 32, 33, 34 or 35, wherein the hydrophilic spacer B comprise at least one OEG motif, the radical 8-amino-3,6-dioxaoctanic acid, i.e. —NH—(CH$_2$)$_2$—O—(CH$_2$)$_2$—O—CH$_2$—C(O)—.
37. The composition according to any of embodiments 32-36, wherein W has the formula: W$_a$-W$_b$,
wherein W$_a$ is selected from: —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)—, —C(O)—, —C(O)O— and —OC(O)—, and wherein W$_b$) is selected from: —CH$_2$—C$_6$H$_{12}$—C(=O)—, OEG-, -Lys, -Glu, -γ-Glu-, —CH—, —CH—(CH$_2$—SO$_3$H)—C(O)—, —S(O)$_2$—(CH$_2$)$_3$—C(O)— and a valence bond.
38. The composition according any of embodiments 32-36, wherein W is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)—, —C(O)—, —C(O)O—, —OC(O)—, or a valence bond.
39. The composition according to any of the embodiments, wherein the growth hormone albumin binder conjugate is selected from the group of:

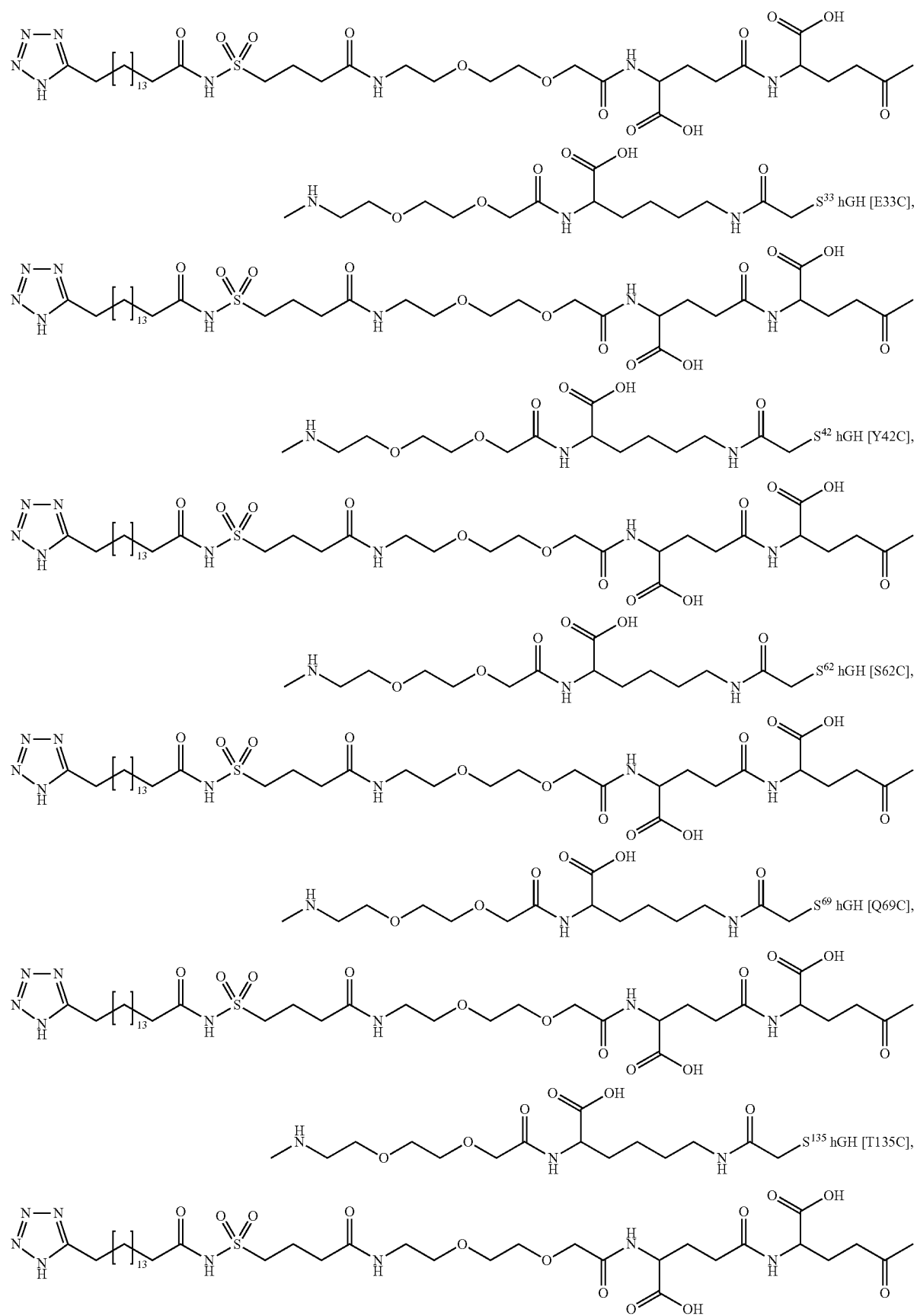

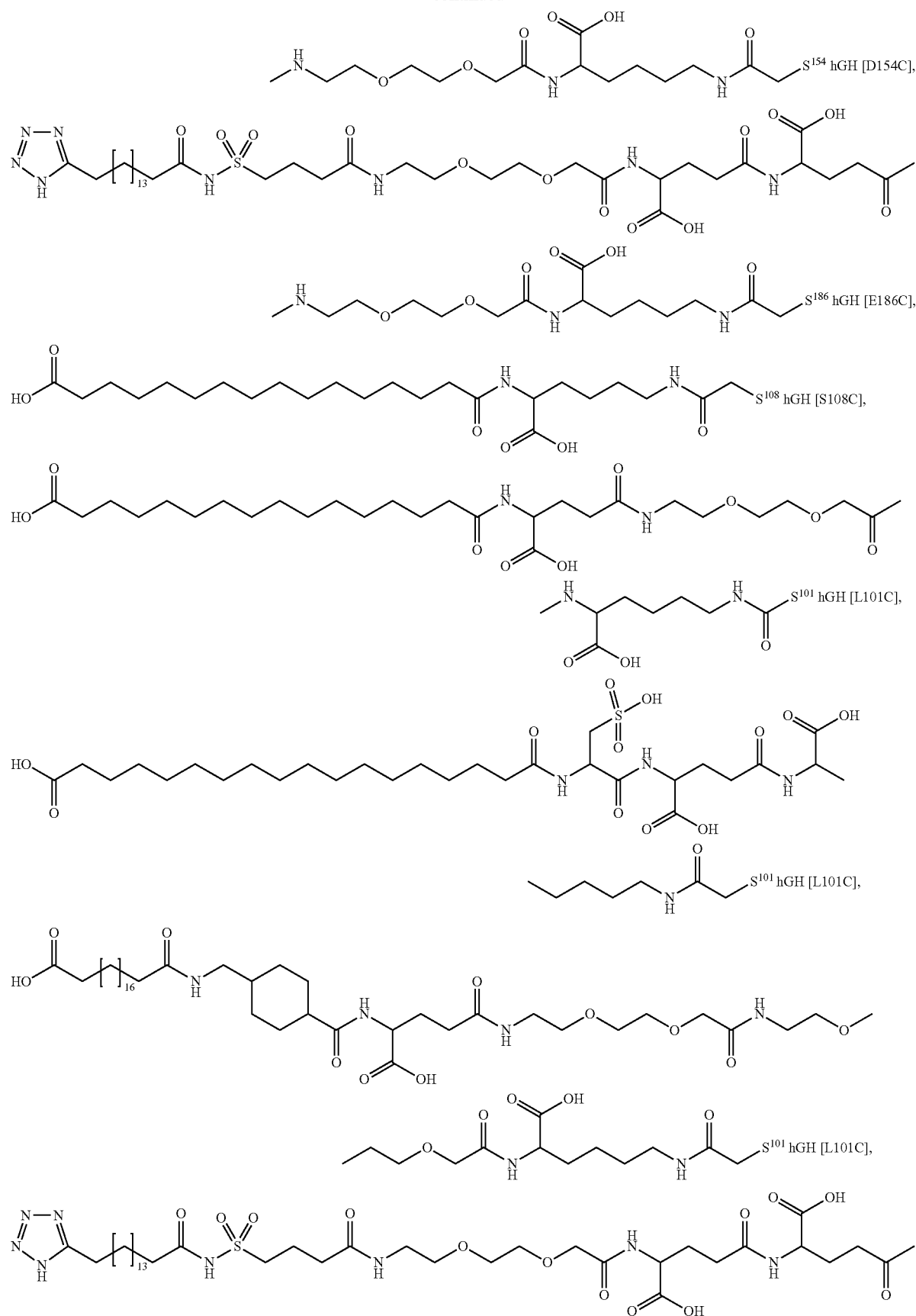

-continued
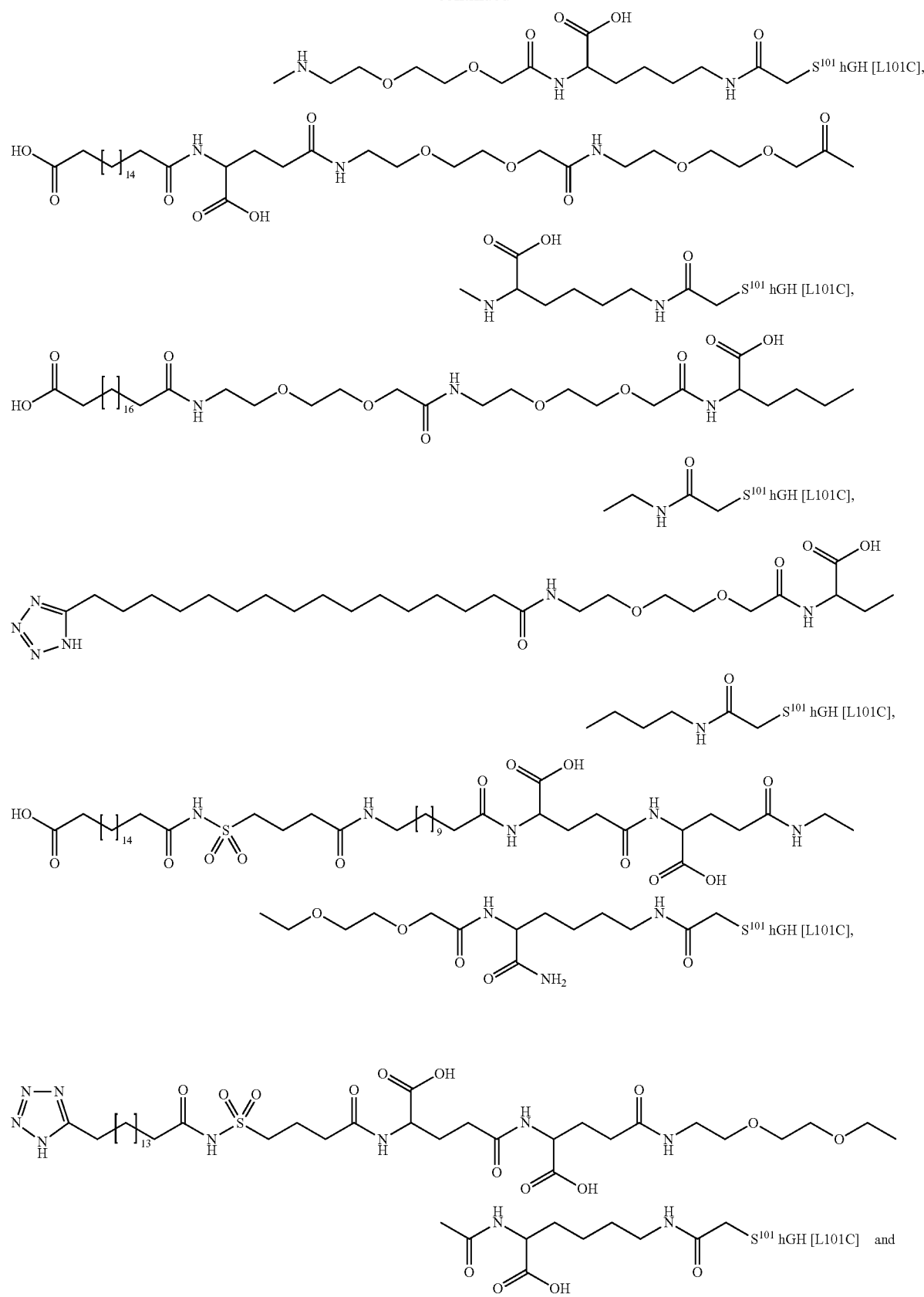

-continued

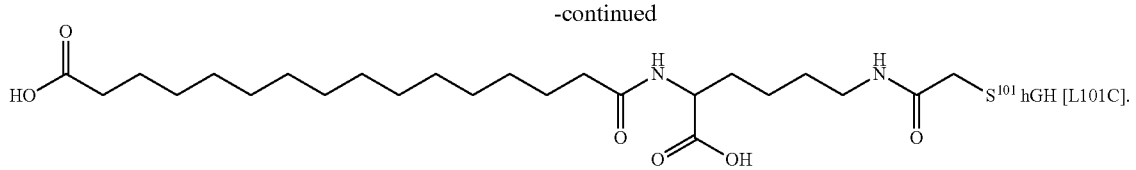

40. The composition according to any of the previous embodiments, wherein the composition is a liquid.
41. The composition according to any of the previous embodiments, wherein the composition is an aqueous composition.
42. The composition according to any of the previous embodiments for use in a method of treatment.
43. The composition according to any of the previous embodiments for use in a method of treatment of growth hormone deficiency.
44. The composition according to any of the previous embodiments for use in a method of treatment for administration by subcutaneous injections.
45. The composition according to any of the previous embodiments for use in a method of treatment for less than daily administration.
46. The composition according to any of the previous embodiments for use in a method of treatment for less than bi weekly administration.
47. The composition according to any of the previous embodiments for use in a method of treatment for once weekly administration.
48. The composition according to any of the previous embodiments for use in a method of treatment for at most once weekly subcutaneous administering.
49. The composition according to any of the previous embodiments comprising 2-20 mg/mL growth hormone albumin-binder conjugate (GH-AB), a buffer, a preservative and 0.5-5.0 mg/mL surfactant.
50. The composition according to any of the previous embodiments wherein the composition comprises 3-10 mg/mL growth hormone albumin binder conjugate.
51. The composition according to any of the previous embodiments for use in a method of treatment for weekly administration of 0.01-0.20 mg/kg, such as 0.02-0.08 mg/kg, of the growth hormone conjugate.
52. The composition according to any of the previous embodiments, wherein the composition is for use in a method of treatment for administering 0.01-0.16 mg/kg of the growth hormone albumin binder conjugate per dosage.
53. The composition according to any of the previous embodiments wherein the composition is for use in a method of treatment of growth hormone deficiency by a once weekly dosage of 0.01-0.08 mg/kg.
54. The composition according to any of the previous embodiments, wherein the composition is for use in a method of treatment by administration to adults.
55. The composition according to any of the previous embodiments wherein the composition is for use in a method of treatment of growth hormone deficiency in adults (AGHD).
56. A pharmaceutical composition comprising a growth hormone albumin binder conjugate, a surfactant selected from poloxamer 188 and 0.5-2 g/mL histidine, 35-50 mg/mL mannitol and 2-5 mg/mL phenol.
57. A pharmaceutical composition comprising a growth hormone albumin binder conjugate, 0.5-2 mg/mL poloxamer 188, 0.5-2 g/mL histidine, 35-50 mg/mL mannitol and 2-5 mg/mL phenol.
58. A pharmaceutical composition comprising
    5-10 mg/mL growth hormone albumin binder conjugate,
    1-3 mg/mL poloxamer 188
    0.5-1.0 mg/mL histidine buffer
    40-45 mg/mL mannitol and
    3-4 mg/mL phenol.
59. A method for preparing a pharmaceutical composition according to any of the previous embodiments.
60. A method for treatment of growth hormone deficiency, comprising administration to a patient in need thereof a therapeutically effective amount of a pharmaceutical composition according to any of the embodiments 1-58.
61. A method for treating diseases or states where the patient may benefit from an increase in the level of circulating growth hormone, the method comprising administering to a patient in need thereof a therapeutically effective amount of a growth hormone albumin-binder conjugate in a pharmaceutical composition according to any of the embodiments 1-58.
62. The method according to embodiment 60, wherein the composition is administered to a patient suffering from adult growth hormone deficiency (AGHD) at most once weekly.
63. The method according to embodiment 60, wherein the composition is administered to a patient suffering from adult growth hormone deficiency (AGHD), wherein 0.01-0.08 mg/kg of the growth hormone albumin binder conjugate is administered per dosage.
64. The method according to embodiment 60, wherein the composition is administered to a patient suffering from adult growth hormone deficiency (AGHD), wherein 0.01-0.08 mg/kg of the growth hormone albumin binder conjugate is administered at most once weekly.
65. The method according to embodiment 60, wherein the composition is administered to a patient suffering from growth hormone deficiency (GHD) once a weekly.
66. The method according to embodiment 60, wherein the composition is administered to a patient suffering from growth hormone deficiency (GHD), wherein 0.01-0.08 mg/kg of the growth hormone albumin binder conjugate is administered per dosage.
67. The method according to embodiment 60, wherein the composition is administered to a patient suffering from growth hormone deficiency (GHD), wherein 0.01-0.08 mg/kg of the growth hormone albumin binder conjugate is administered once a weekly.

68. The method according to embodiment 60, wherein the composition is administered to an adult patient at most once weekly.
69. The method according to embodiment 60, wherein the composition is administered to a patient suffering from growth hormone deficiency in adults (AGHD) at most once weekly.
70. The method according to embodiment 60, wherein the composition is administered to a patient suffering from growth hormone deficiency in adults (AGHD), wherein 0.01-0.08 mg/kg of the growth hormone albumin binder conjugate is administered per dosage.

EXAMPLES

A growth hormone albumin binder conjugates may be prepared according to standard methods. The growth hormone protein is expressed in a suitable host, such as *E. coli* and purified. The conjugation reaction may be performed according to methods in the art know to the skilled person. General methods useful for preparing such conjugates are presented below including details relating to the specific conjugates described herein. The skilled person may adapt the methods to prepare alternative conjugates based on general knowledge in the art.

General Method for Preparing a Growth Hormone Protein

The gene coding for a growth hormone protein is inserted recombinant into a plasmid vector. A suitable *E. coli* strain is subsequently transformed using the plasmid vector. Human GH or GH variants may be expressed with an N-terminal methionine or as a MEAE fusion from which the MEAE sequence is subsequently cleaved off.

Cell stock are prepared in 25% glycerol and stored at −80° C. Glycerol stock strain are inoculated into LB plates and subsequently incubated at 37° C. overnight. The content of each plate is washed with LB medium and diluted into 500 mL LB medium for expression. The cultures are incubated at 37° C. with shaking at 220 rpm until $OD_{600}$ 0.6 has reached. Succeeding induction is performed using 0.2 mM IPTG at 25° C. for 6 hours. Cells are finally harvested by centrifugation.

Cells are subsequently suspended in 10 mM Tris-HCl, pH=9.0 containing 0.05% Tween 20, 2.5 mM EDTA and 4M urea, and disrupted using a cell disrupter at 30 kPSI. If a GH molecule with a free cysteine (for conjugation) is expressed 10 mM cysteamine is included in the suspension buffer. The supernatant was collected by centrifugation and subsequently subjected to chromatographic purification.

The purification is performed using ion-exchange chromatography and hydrophobic interaction, followed by removal of the peptide tag using human dipeptidyl peptidase I (hDPPI) expressed from CHO cell. Final purification is achieved by isoprecipitation and ion-exchange chromatography.

The purification could also be achieved by using but not limited to ion-exchange chromatography, hydrophobic interaction chromatography, affinity chromatography, size exclusion chromatography and membrane based separation techniques known to a person skilled in the art.

Preparation of Single Cys GH Variants Including GH(L101C):

After the initial purification as described above, the variants may have part of its free cysteine blocked with glutathione and cystamine. De-blocking is performed enzymatically using glutaredoxin II (Grx2) in an equilibrium buffer containing GSH and GSSG. De-blocked GH (L101C) is separated from low molecular weight GSH/GSSG by buffer exchanged on a Sephadex G25 column.

Protein Chemical Characterization of Purified Growth Hormone Compounds.

The intact purified protein is analysed using MALDI-MS to confirm that the observed mass corresponded to the theoretical mass deduced from the amino acid sequence.

The expected linkage disulfide bonds may be demonstrated by peptide mapping using trypsin and AspN digestion followed by MALDI-MS analysis of the digest before and after reduction of the disulfide bonds with DTT.

Albumin-Binder Side-Chain Preparation

Side Chain (I)

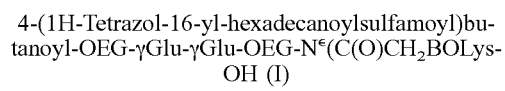

4-(1H-Tetrazol-16-yl-hexadecanoylsulfamoyl)butanoyl-OEG-γGlu-γGlu-OEG-N$^\epsilon$(C(O)CH$_2$BOLys-OH (I)

(I)

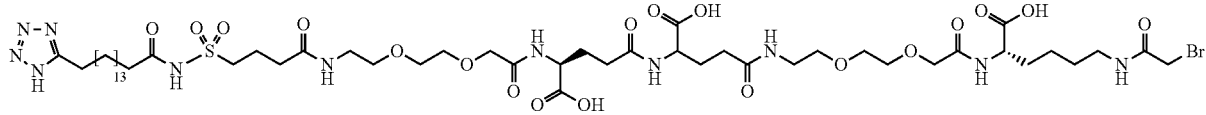

The side-chain (I) was synthesised on solid support according to scheme 1, in 1 mM scale using standard Fmoc-peptide chemistry on an ABI433 synthetizer. Peptide was assembled on a Fmoc-Lys(MTT)-Wang resin using Fmoc-OEG-OH and Fmoc-Glu-OtBu protected amino acids. 4-(16-1H-Tetrazol-5-yl-hexadecanoylsulfamoyl)butyric acid was manual coupled using DIC/NHS in DCM/NMP, 2 eq. over-night, TNBS test showed the reaction to be completed. The resin was then treated with 50 mL DCM/TFA/TIS/water (94:2:2:2) in a flow-through arrangement until the yellow colour disappeared, ~20 min. followed by washing and neutralizing with DIPEA/DMF. Bromo acetic acid (4 mM) in DCM/NMP (1:1) was activated with a 1 mM mixture of NHS and DIC, filtered and added to the resin with addition of further 1 mM of DIPEA. After 1 hr the reaction was completed. The resin was treated with 80 mL TFA/TIS/water (95:2,5:2,5) for 1 hr. Evaporated with a stream of N$_2$, precipitated by addition of Et$_2$O and washed with Et$_2$O and dried. Crude product was purified on preparative HPLC (2 runs), with a gradient from 30-80% 0, 1 TFA/MeCN against 0, 1% TFA in water. Fractions were collected and lyophilized with ~50% MeCN affording side chain (I). TOF-MS: mass 1272.52 (M+1)

Scheme 1

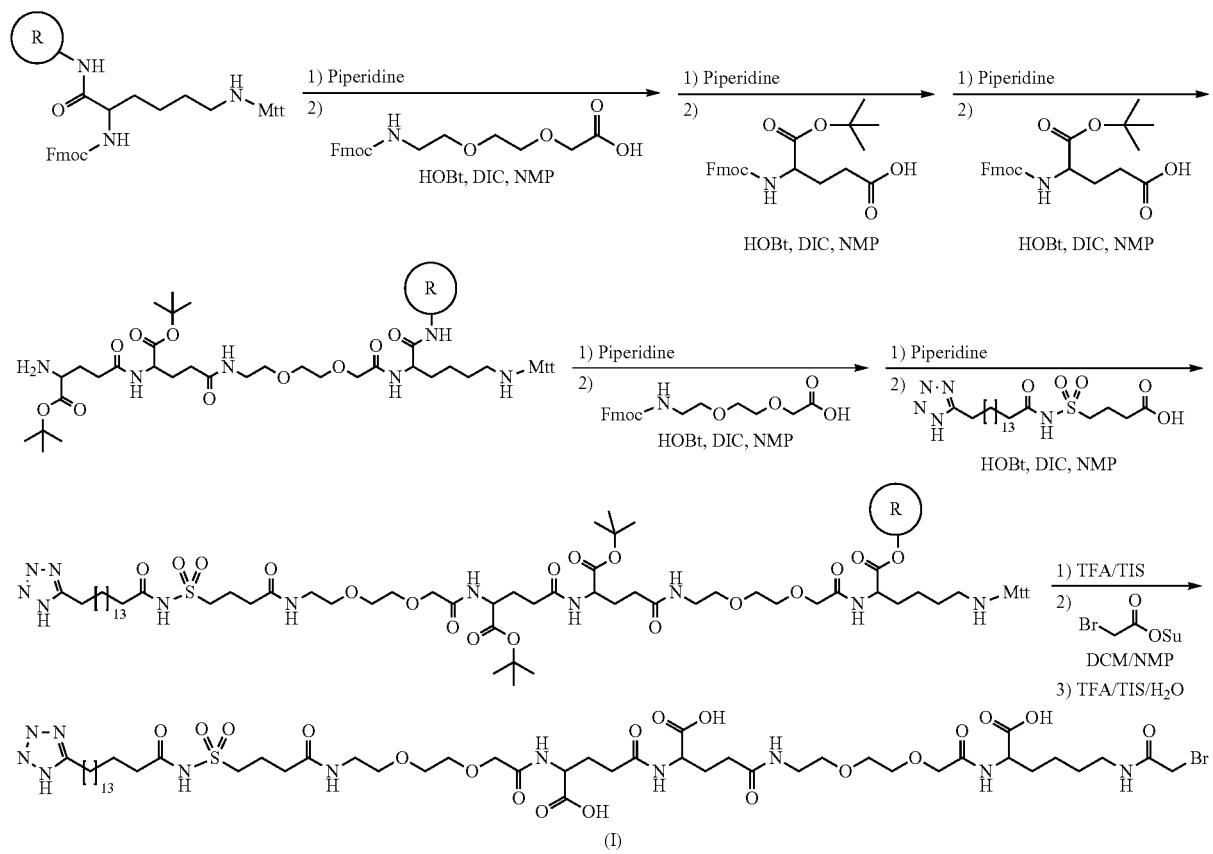

Side Chain (II)

In a similar way as described in above the following side chain (II) was prepared using Fmoc-Lys(Mtt)-OH and Wang Resin. TOF-MS: mass 844.84 (M+1)

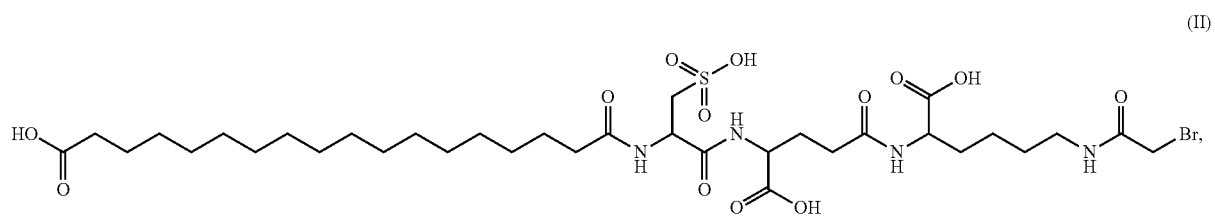 [SMILES: O=C(O)CCCCCCCCCCCCCCCCC(=O)NC(CS(=O)(=O)O)C(=O)NC(CCC(=O)NC(CCCCNC(=O)CBr)C(=O)O)C(=O)O]

General Method for Conjugating an Albumin Binder Side-Chain to a Growth Hormone Protein Coupling of a GH protein having an internal free single cys (GH-SH) with an albumin binding side-chain (AB-Halo) as described above.

a) Liberation of GH-SH (VII) via reduction of disulfide (VI) with a suitable selective reducing agent:
b) Alkylation of free GH-SH (VII) with a halogen activated albumin binder (VIII) affording growth hormone conjugate with AB linked to "—S—" of single Cys residue.

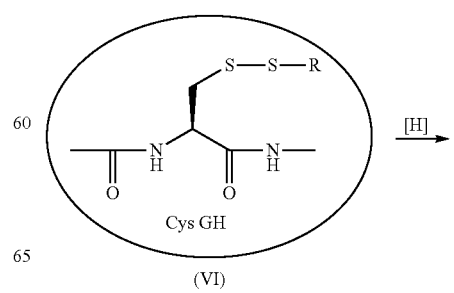

-continued

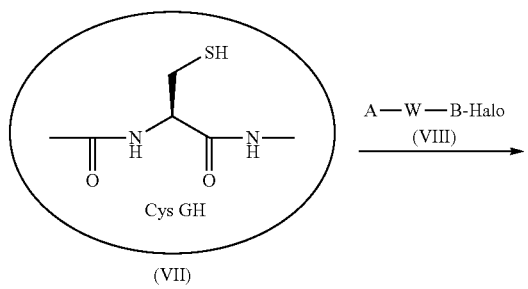

(VII)

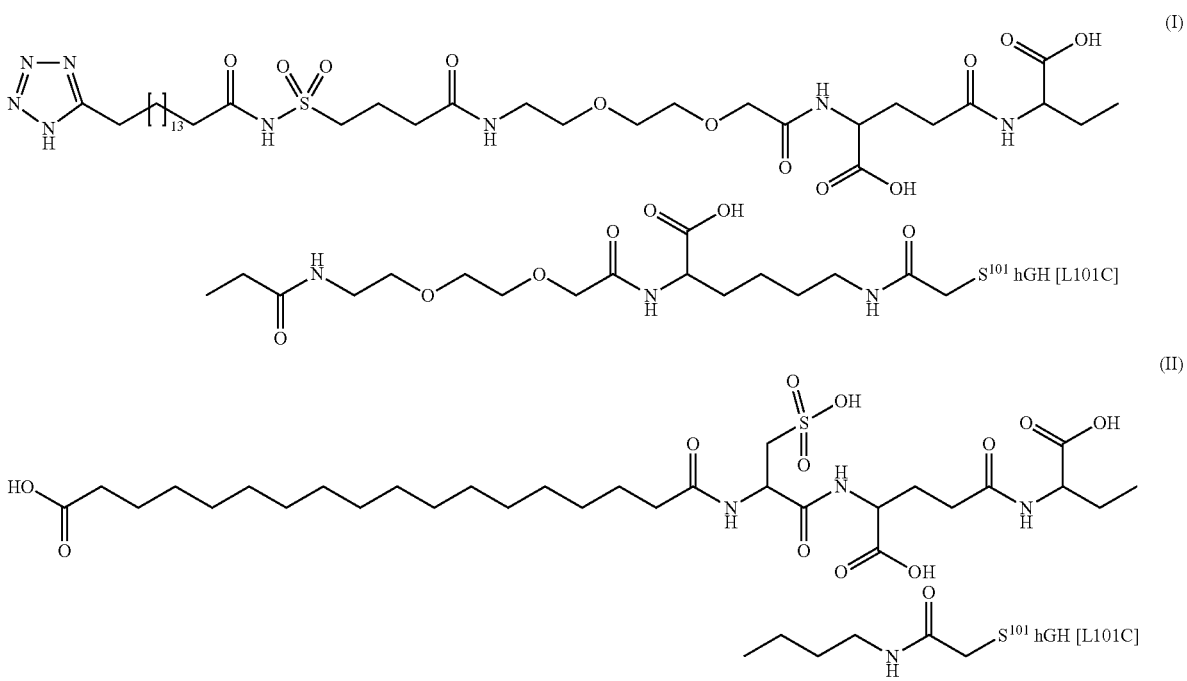

R-cyclodextrin and added MTP (2.1 mL, 1%) and 0.5 M NaCl (6.34 g). To this mixture was added concentrated GH(L101C) (1 eq, 46 mL) and the mixture was left over night at RT. The solution became cloudy overnight. As HPLC indicated unreacted starting material another 5 eq. albumin binder from example 5 dissolved in a minimum of NMP was added. The resulting mixture was stirred at RT for an additional 16 hrs. For further details on conjugation and purification method reference is made to WO 11/089255.

Growth hormone albumin-binder conjugate I and II, shown below, was obtained using the method described above.

Alternative methods may be used to prepare alternative growth hormone albumin-binder conjugates as have previously been described in WO11/015649 including N-terminal C-terminal conjugations and in chain site specific conjugations to Gln or Lys residues using a transglutaminase reaction. Also for single Cys conjugation as described above an alternative conjugation process can be applied, such as described in WO11/050923.

Determination of HMWP Content by Size-Exclusion Chromatography (SEC-HPLC)

The analytical procedure is a size-exclusion chromatography (SE-HPLC) test, where the samples are analysed using a TSK G2000 SWxl column, isocratic elution using a sodium phosphate/isopropanol buffer and subsequent UV detection at 215 nm. % HMWP is calculated relative to the total integrated area Visual Inspection Samples (minimum volume of 2 mL) stored in glass vials or cartridges (type I) are inspected under architect lamp and in light chamber. The visual appearance of samples is quantified by a visual score with criteria for clarity and particles on a score from 1 to 5 with 1 being clear and without particles and 5 referring to samples with visible precipitate.

-continued

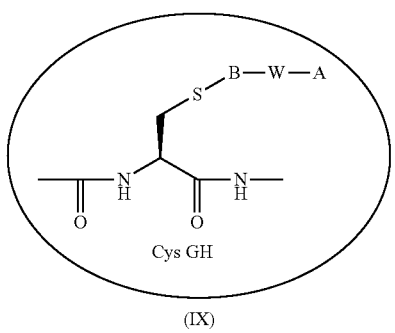

(IX)

Conjugation of Albumin Binder Side Chain with GH (101C) with Side Chain (I)

The albumin binder side chain (78 mg/5 eq) is dissolved in 170 mL HEPES/EDTA buffer with 5% hydroxypropyl- Determination of Protein Aggregates Using Optical Density (OD)

The optical density of samples is measured at 340 nm using a Varian Cary 100 Bio UV-VIS spectrophotometer.
Determination of Particles Using Micro-Flow Imaging (MFI)

Quantification of particles by size and morphology in undiluted solution (1 mL) was performed using flow microscopy on Micro-Flow Imaging flow microscopy MFI 5000. Quantification and characterisation of sub-visible particles >2 μm, >10 μm and >25 μm was performed. A filter (circularity 0-0.85) removing eventual air bubbles and silicon droplets, was also applied.

Example 1

The stability of a formulation of Conjugate I, described above was investigated at different pH (pH 6.0 and 6.6) including different surfactants and variation of surfactant and buffer (histidine) concentration. The study was performed as a design of experiment (DoE) study.

The formulation tested includes in addition to growth hormone conjugate I a surfactant and histidine buffer in a concentration of 0.68 mg/mL or 1.55 mg/mL, also including 40 mg/mL mannitol and 3.0 mg/mL phenol.

The amount of HMWP (high molecular weight protein) was measured over 90 days, in samples from time point 0, 30, 60 and 90 days at 5° C. Similar data were obtained at 25° C. The HMWP content is measured by size-exclusion chromatography (SEC-HPLC) using a TSK gel G3000 SWXL column, a sodium phosphate/isopropanol pH 7.0 mobile phase with isocratic elution and subsequent UV detection at 215 nm.

FIG. 1 shows that poloxamer 188 stabilises the formulation at the time of preparation. Increased amounts of HMWP were found at time zero (t=0) in formulations without poloxamer 188. The level of HMWP in polysorbate 80 formulations and formulations without surfactant was however decreased to levels comparable to formulations with poloxamer analysed after one month storage at 5° C.

Figure 2:
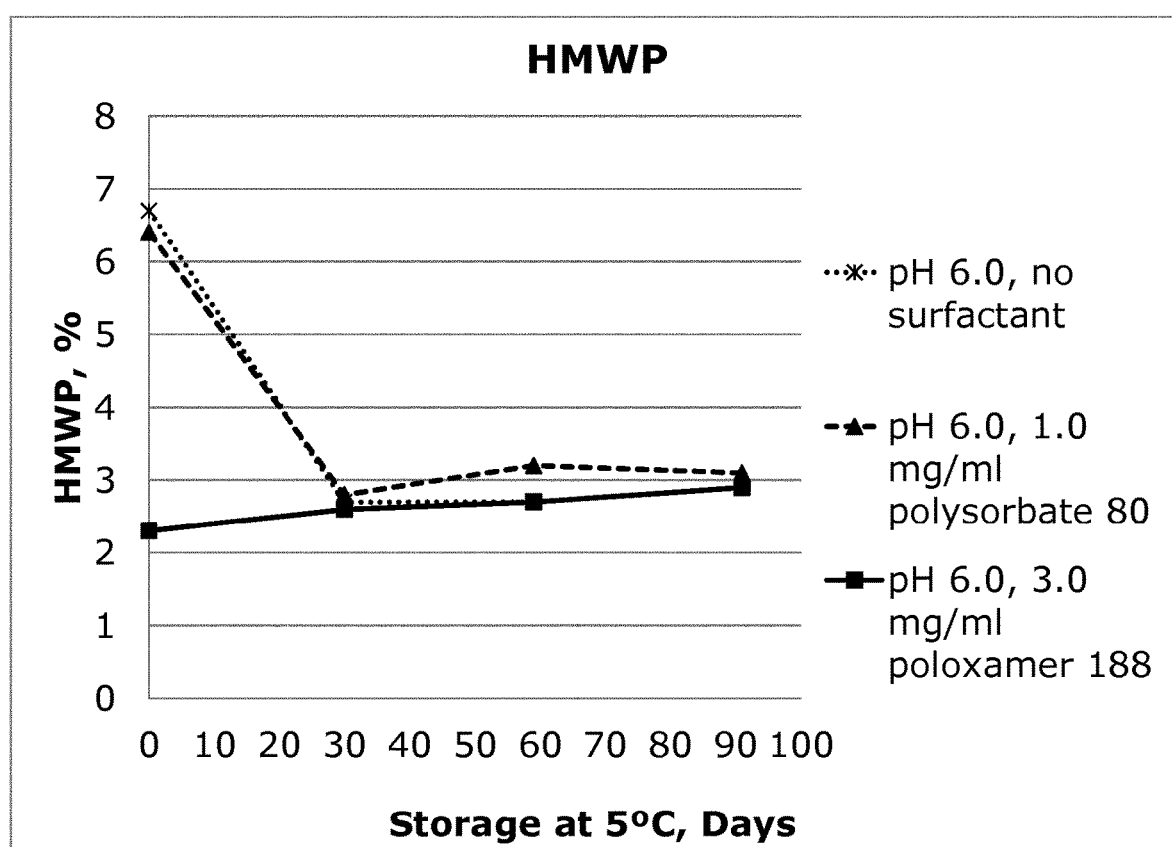
FIG. 2 shows the HMWP content in pharmaceutical compositions comprising various surfactants in different concentration in compositions with pH 6.0. The HMWP content as measured during storage at 5° C. for a period of 90 days is shown.

FIG. 2 shows that 3 mg/mL poloxamer 188 is superior to 1.0 mg/mL polysorbate 80 at low pH.

Example 2

A manufacturability study was performed preparing formulations of conjugate I.

| Conjugate I | histidine, | mannitol | phenol | poloxamer | pH |
|---|---|---|---|---|---|
| 6.7 mg/mL | 0.68 mg/mL | 44 mg/mL | 3.0 mg/mL | from 0 to 3.0 mg/mL | 6.8 |

The liquid conjugate I drug substance preparation (including histidine buffer) was pH adjusted to pH 6.5 and 7.1 in a volume approximately 40% of final volume. The buffer solution (histidine, mannitol, poloxamer and phenol) of approximately 60% volume was pH adjusted to pH 6.8. After mixing of the two solutions the final formulation was pH adjusted to pH 6.8. Formulations at pH 6.8, prepared from preparations having different pH's, were followed in a stability study during 1 month storage at 25° C.

Samples taken at time=0, 1 day, 2 weeks and 1 month was analyzed

All samples appeared clear from visual inspection and % HMPW measured from SE-HPLC is provided in the table below.

TABLE 1

Evaluation of conjugate I formulation, pH 6.8

| pH of conjugate I preparation | Poloxamer 188 (mg/mL) | T = 0 25° C. | T = 1 day 25° C. | T = 2 weeks 25° C. | 1 = month 25° C. |
|---|---|---|---|---|---|
| pH 6.5, | 0 | 3.6 | 3.6 | 4.1 | 4.7 |
| pH 6.5 | 0.5 | 3.6 | 3.5 | 3.9 | 4.5 |
| pH 6.5 | 1.0 | 3.5 | 3.8 | 4.6 | 5.1 |
| pH 6.5 | 3.0 | 3.5 | 3.8 | 4.6 | 5.1 |
| pH 7.1 | 0 | 3.6 | 3.6 | 3.9 | 4.5 |
| pH 7.1 | 0.5 | 3.5 | 3.6 | 4.2 | 4.7 |
| pH 7.1 | 1.0 | 3.5 | 3.5 | 4.1 | 4.6 |
| pH 7.1 | 3.0 | 3.5 | 3.5 | 4.1 | 4.6 |

No clear difference in the levels of HMWP was observed between the formulations dependent on pH of the GH conjugate DS solutions during preparation of final product formulations. All formulations display a similar level of HMWP at time of preparation and similar stability in the accelerated stability study where stability during 1 month storage at 25 C was tested. A slight tendency for the formulations with higher amounts of poloxamer 188 (1.0 mg/mL and 3.0 mg/mL) to develop a higher amount of HMWP over time might be observed for the formulations prepared from DS with pH 6.5.

The almost similar stability of all formulations is expected to be caused by an nearly comparable pH in formulations after mixing of buffer and DS solutions as the buffer solution (pH 6.8) comprises approximately 60% of the final product solution.

Example 3

Formulations of Conjugate I were made with variation in concentration of poloxamer 188 (1.0, 3.0 and 5.0 mg/mL) in histidine buffer including mannitol and phenol (0.68 mg/mL histidine, 44 mg/mL mannitol, and 3 mg/mL phenol). Stability at 30° C. at pH 6.2, 6.8 and 7.4 was tested by measuring HMWP. The study was performed as a design of experiment (DoE) study.

Figure 3:
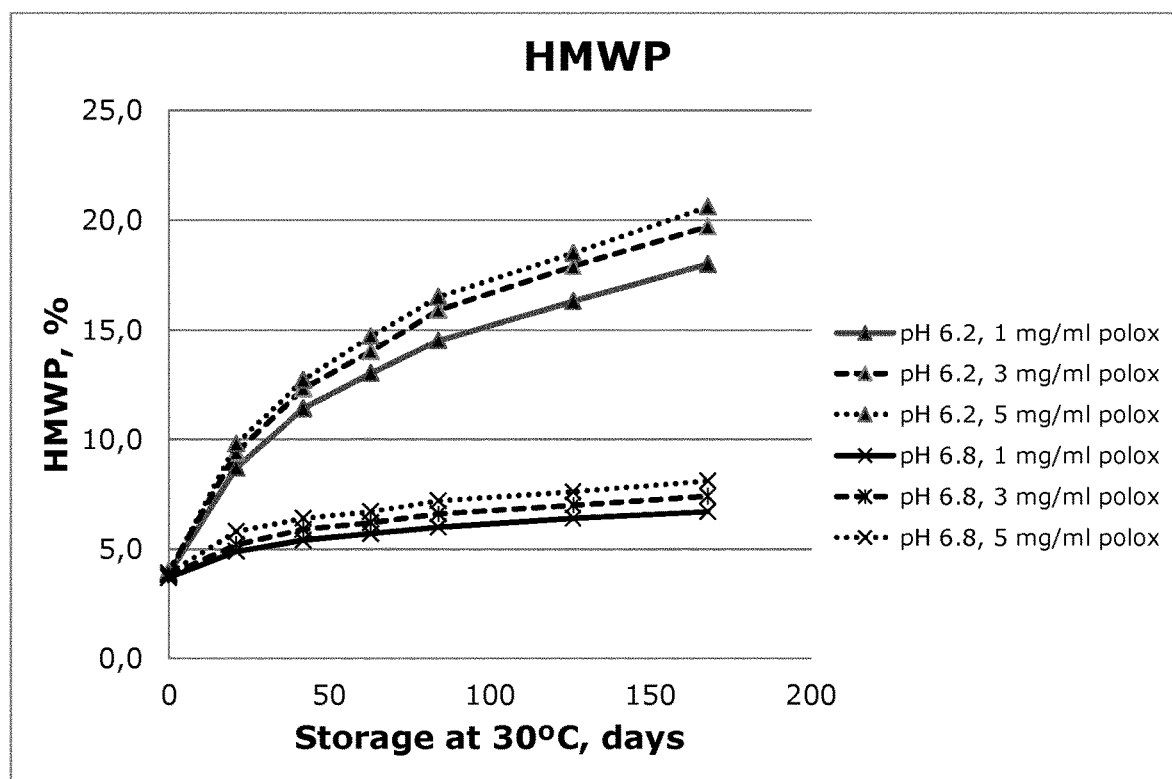
FIG. 3 shows the HMWP content in a series of compositions with various amount of surfactant (poloxamer 188) at pH 6.2 and 6.8. The HMWP content as measured during storage at 30° C. for a period of 180 days is shown.

As seen in FIG. 3, the samples displayed an equal amount of HMWP at time 0. (T=0). The statistical analysis of HMWP data found no significant effect of poloxamer after 4 weeks storage at 30° C. However, a tendency for formulation with increased amount of poloxamer to develop a higher amount of HMWP over time was observed at both pH 6.2 and 6.8, indicating that the high concentration of poloxamer 188 should be avoided if the composition is for long term storage. Data from pH 7.4 is not included in figure as pH effect is dominating resulting in a generally low HMWP formation.

Example 4

The effect at pH 6.2, 6.5 and 6.8 was studied in the following experiment. Conjugate I formulations were made with variation in concentration of poloxamer 188 (0.0, 1.0, 3.0 mg/mL) and with variation in pH (6.2, 6.5 and 6.8). Other components of the tested compositions were as in Example 3. Samples were physically stressed with shear at room temperature for 7 days. Samples were taken after 3 and 6 hours and after 1, 2, 5, 6 and 7 days. Other samples were stressed by pipetting 25 times. All samples were visually examined and further analysed for OD (optical density) at 340 nm.

Figure 4:
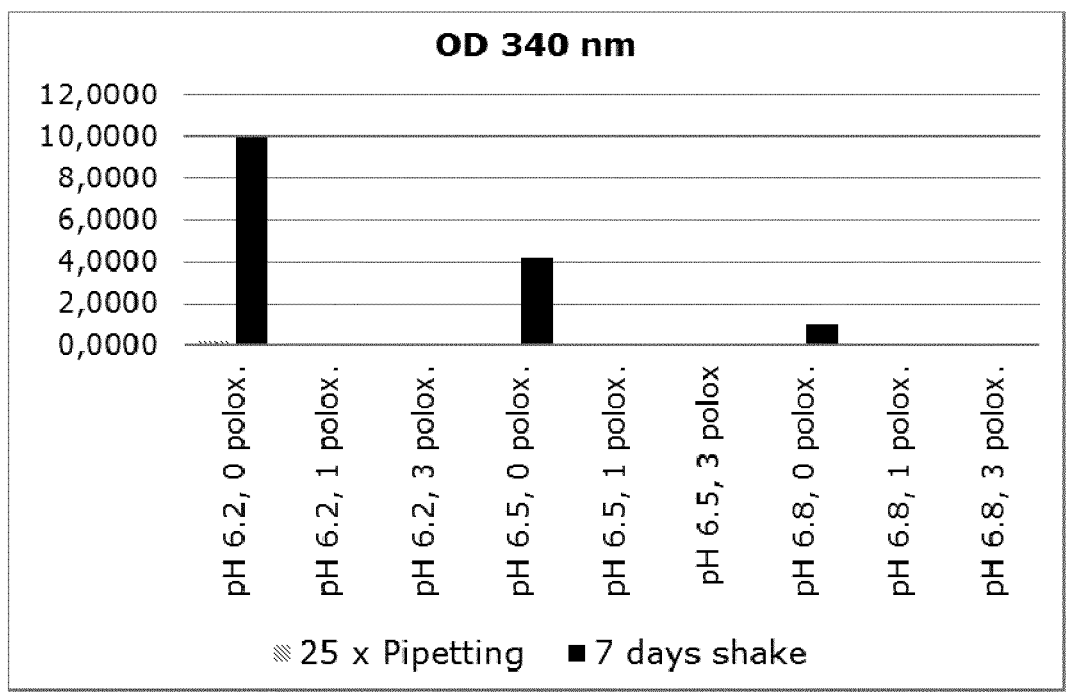
FIG. 4 shows OD at 340 nm of a series of pharmaceutical compositions comprising various amounts of poloxamer (0, 1.0, 3.0 mg/mL) and with variation in pH (6.2, 6.5 and 6.8) after physically stress (pipetting and shaking). The figures A and B represent the same data but with focus on different parts of the left axis as B is an enlargement of the low range to visualize low range measurements.
Figure 4:
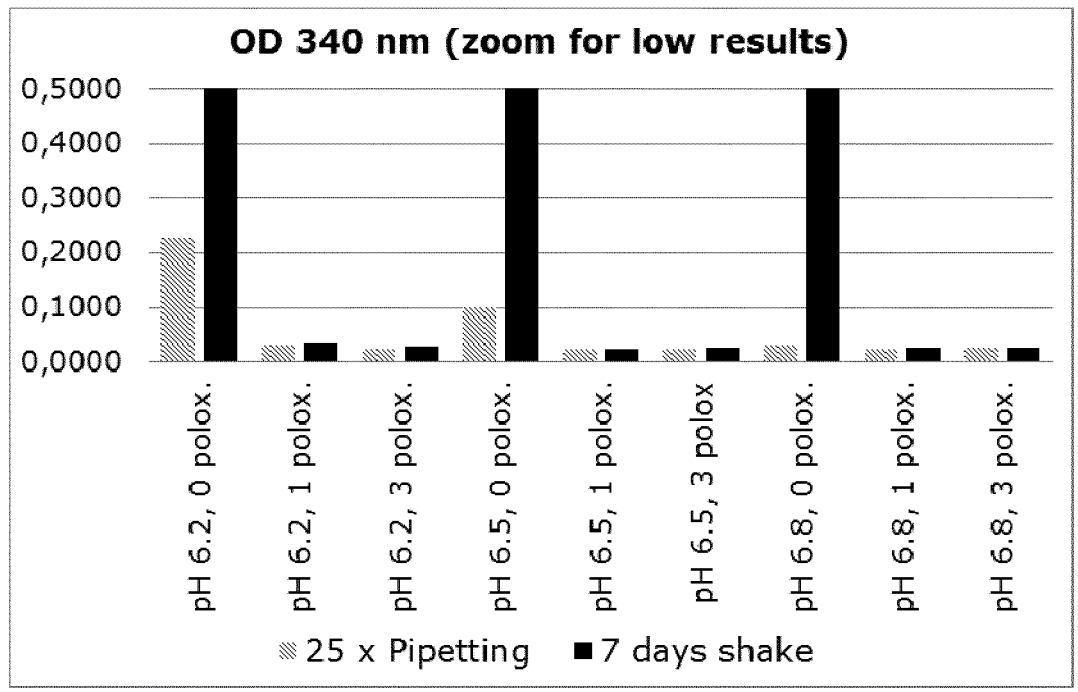

As seen in FIG. 4, samples without poloxamer 188 displayed a distinct increase in OD 340 compared to samples with 1.0 and 3.0 mg/mL poloxamer 188 in both shaking and pipetting study. The tendency was confirmed at all pH levels. FIG. 4A display the full results whereas FIG. 4B display only the low OD 340 measure. Furthermore, the visual scoring clearly showed that samples without poloxamer were turbid and the turbidity increased at decreasing pH.

Example 5

Figure 5:
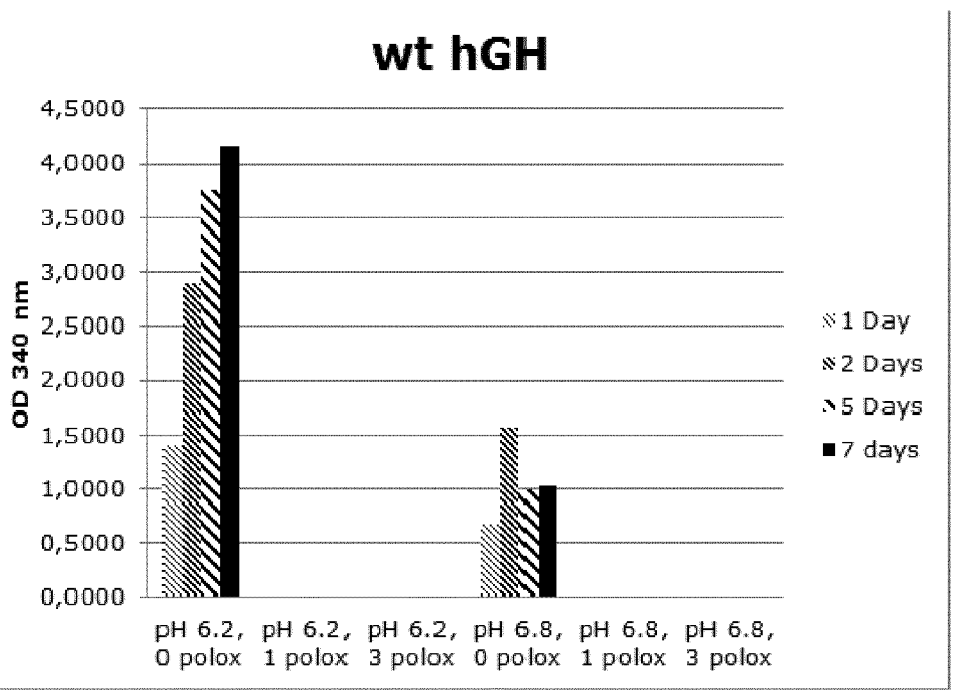
FIG. 5 shows OD at 340 nm of series of pharmaceutical compositions comprising different growth hormone compounds, which are WT hGH, GH L101C, and Conjugate I.
Figure 5:
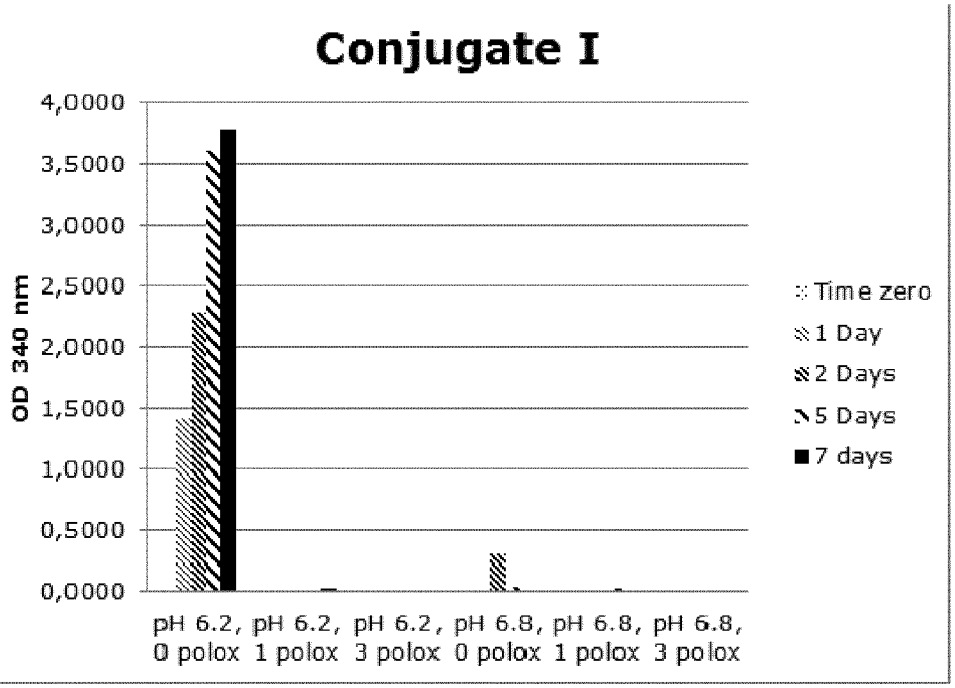

Experiments similar to Example 4 at pH 6.2 and 6.8 were performed using three additional growth hormone compounds. Wild type human growth hormone (WT hGH), Conjugate I and a growth hormone variant including a 101 Cys mutation (GH L101C) which is also the GH protein of Conjugate I. As seen from FIGS. 5A, 5B and 5C the conclusions from above were confirmed. Low surfactant content improves the stability of the composition both initially and after stress as tested during 7 days. For Conjugate I, samples without poloxamer seemed specifically dependent on pH. By visual scoring, an increase of turbidity was observed with decreasing pH.

Example 6

Micro-flow Imaging (MFI) evaluation was used to measure particle formation in growth hormone compositions. Samples (1 mL) were measured on Micro-Flow Imaging flow microscopy MFI 5000. As above the following compounds were included in the evaluation: Wild type human growth hormone (hGH), Conjugate I, Conjugate II and growth hormone variant L101C (GH L101C).

The stabilising effect of poloxamer 188 is evaluated with 6.7 mg/mL growth hormone compound at pH 6.2 and pH 6.8.

The study is set up as a stress stability study with shaking samples for up to 7 days at room temperature. Growth hormone compositions at pH 6.2 and 6.8 including 0.0, 1.0 or 3.0 mg/mL poloxamer 188 and measurements were made at T=0 and T=2 (2 days). The compositions all comprised 0.68 mg/mL histidine, 44.0 mg/mL and 3 mg/mL phenol. Data obtained at T=0 is included in table 1, while data obtained after two days (T=2) is included in table 2, below.

TABLE 1

Particle numbers at T = 0

| Compound (6.7 mg/mL) | pH | Poloxamer (mg/mL) | >2 µm (#/mL) | >10 µm (#/mL) | >25 µm (#/mL) |
|---|---|---|---|---|---|
| hGH | 6.2 | 0.0 | 108622 | 25593 | 5645 |
| hGH | 6.2 | 1.0 | 1012 | 195 | 33 |
| hGH | 6.2 | 3.0 | 451 | 131 | 41 |
| hGH | 6.8 | 0.0 | 45695 | 7568 | 1186 |
| hGH | 6.8 | 1.0 | 317 | 141 | 39 |
| hGH | 6.8 | 3.0 | 268 | 127 | 47 |
| Conjugate I | 6.2 | 0.0 | 52825 | 11045 | 2117 |
| Conjugate I | 6.2 | 1.0 | 1234 | 348 | 88 |
| Conjugate I | 6.2 | 3.0 | 119 | 29 | 6 |
| Conjugate I | 6.8 | 0.0 | 1558 | 192 | 18 |
| Conjugate I | 6.8 | 1.0 | 213 | 82 | 39 |
| Conjugate I | 6.8 | 3.0 | 76 | 23 | 6 |
| GH L101C | 6.2 | 0.0 | 56467 | 11807 | 2008 |
| GH L101C | 6.2 | 1.0 | 2020 | 488 | 78 |
| GH L101C | 6.2 | 3.0 | 1195 | 88 | 12 |
| GH L101C | 6.8 | 0.0 | 26262 | 3472 | 477 |
| GH L101C | 6.8 | 1.0 | 1575 | 242 | 43 |
| GH L101C | 6.8 | 3.0 | 106 | 37 | 14 |

TABLE 2

Particle numbers at T = 2. N/A indicates that it was not possible to measure particle number due to too many particles.

| Compound (6.7 mg/mL) | pH | Poloxamer (mg/mL) | >2 µm (#/mL) | >10 µm (#/mL) | >25 µm (#/mL) |
|---|---|---|---|---|---|
| hGH | 6.2 | 0.0 | n/a | n/a | n/a |
| hGH | 6.2 | 1.0 | 3460 | 807 | 188 |
| hGH | 6.2 | 3.0 | 200 | 107 | 20 |
| hGH | 6.8 | 0.0 | n/a | n/a | n/a |
| hGH | 6.8 | 1.0 | 14204 | 1791 | 133 |
| hGH | 6.8 | 3.0 | 411 | 129 | 51 |
| Conjugate I | 6.2 | 0.0 | n/a | n/a | n/a |
| Conjugate I | 6.2 | 1.0 | 2168 | 503 | 84 |
| Conjugate I | 6.2 | 3.0 | 214 | 64 | 18 |
| Conjugate I | 6.8 | 0.0 | 89085 | 5095 | 60 |
| Conjugate I | 6.8 | 1.0 | 310 | 86 | 16 |
| Conjugate I | 6.8 | 3.0 | 82 | 18 | 4 |
| GH L101C | 6.2 | 0.0 | 301980 | 29499 | 3583 |
| GH L101C | 6.2 | 1.0 | 1119 | 283 | 47 |
| GH L101C | 6.2 | 3.0 | 922 | 306 | 92 |
| GH L101C | 6.8 | 0.0 | 40493 | 6443 | 1025 |
| GH L101C | 6.8 | 1.0 | 775 | 128 | 31 |
| GH L101C | 6.8 | 3.0 | 150 | 18 | 2 |
| Conjugate II | 6.2 | 0.0 | 263980 | 33209 | 3549 |
| Conjugate II | 6.2 | 3.0 | 512 | 159 | 58 |
| Conjugate II | 6.8 | 0.0 | 19818 | 3278 | 506 |
| Conjugate II | 6.8 | 3.0 | 483 | 188 | 55 |

It was concluded that poloxamer 188 suppresses particle formation in all growth hormone compound composition tested. Moreover, higher concentration (3 mg/mL compared to 1 mg/mL) of poloxamer 188 has a stronger effect on particle formation. For the conjugates of GH, pH seems to have a pronounced effect on particle suppression as better results are obtained at pH 6.8 than at pH 6.2, reducing the advantage of a high poloxamer concentration. A similar conclusion was reached by visual inspection.

Example 7

A randomised, double-blind, placebo-controlled multiple-dose and dose-escalation trial was performed in Japanese and non-Asian healthy, male subjects, to evaluate safety, tolerability and pharmacokinetic (PK) and pharmacodynamic (PD) parameters.

Four cohorts of 16 subjects were dosed by subcutaneous administration with conjugate 1 (n=12) or placebo (n=4) once-weekly for 4 consecutive weeks (equal numbers of Japanese and non-Asian subjects). The dosage was 0.02, 0.08, 0.16 and 0.24 mg/kg in the individual cohorts, The compound was provided as freeze dried formulation and reconstituted before use.

The pharmacokinetic of conjugate I was assessed after the fourth ($4^{th}$) dose. A dose-dependent increase of the mean plasma concentrations of conjugate 1 was observed (data not shown). The pharmacodynamics parameters of conjugate I administration was evaluated by measuring the IGF-I response (Immunodiagnostic system (IDS)).

Dose-dependent IGF-I and IGFBP-3 responses were observed, with elevated IGF-I levels at all doses. The mean IGF-I standard deviation score (SDS) profiles (FIG. 6) indicate that conjugate I may be suitable for once-weekly dosing. If further shows that a clinically relevant IGF-I response was induced at doses ≤0.08 mg/kg.

Example 8

The pharmaceutical composition may be prepared by mixing a preparation of the growth hormone albumin-binder conjugate with the required excipients. The following process is useful when a liquid preparation of the conjugated is the starting point.

Final Composition:

Growth hormone conjugate I (6.7 mg/ml)

1.0 mg/ml poloxamer 188

0.68 mg/ml histidine 44 mg/ml mannitol 4.0 mg/ml phenol pH for the formulation is 6.8

Stock Solutions:

21.3 and 20.5 mg/ml Growth hormone conjugate I (in 0.68 mg/ml histidine) (batch NLfK040501 and NLfK040503)

20 mg/ml poloxamer 188 (in WFI)

Buffer solution: 110 mg/ml mannitol, 10 mg/ml phenol and histidine, wherein the histidine concentration is dependent on the volume/amount of DS used.

HCl for pH adjustment

The conjugate I preparations (including histidine buffer) was weighed out and poloxamer 188 was added as a stock solution. WFI was added to the solution to reach 55% of final volume. A buffer solution was prepared including mannitol, histidine, phenol and hydrochloric acid for adjustment of pH. The buffer solution (40% of final volume) was added to the conjugate I and poloxamer 188 solution resulting in 95% of final volume. pH was measured (and adjusted if necessary), and finally WFI was added to reach the final volume.

During preparation samples were taken from the conjugate I and poloxamer 188 solution and from the intermediate formulation and the final pharmaceutical composition. The content of high molecular weight proteins (% HMWP) was measured by SE-HPLC (table 1) and was found to be low throughout the process. The final pharmaceutical composition appeared clear and colourless.

TABLE 1

HMWP (%) of Conjugate 1 preparations. in-process samples and final formulation

| | Conjugate I preparation batch NLfK040501 | Conjugate I preparation batch NLfK040503 | Conjugate I and poloxamer 188 solution (55% of final volume) | Intermediate formulation 95% of final volume | Final formulation |
|---|---|---|---|---|---|
| HMWP (%) | 1.2 | 3.5 | 2.0 | 1.9 | 1.9 |

Example 9

In another study phenol was included in a phenol-buffer solution at varying concentrations (5, 10 and 30 mg/ml) and introduced to the conjugate I preparation. As seen below use of 30 mg/ml phenol gave an increase in % HMWP in the final formulation. The level of HMWP is dependent on the concentration of conjugate I in the solution and the concentration of phenol.

Stock Solutions and Excipients:

Conjugate I preparation (batch IHJe12-021): 18.0 mg/ml

Phenol solutions 30 mg/ml, 10 mg/ml and 5 mg/ml 50 mg/ml poloxamer

Mannitol (powder).

Histidine

For each formulation a phenol and histidine solution was prepared including the total amount of phenol and histidine to reach the desired concentration in the final formulation.

Conjugate I preparation, in amount to reach total amount in final formulation, was added to the phenol-histidine solutions, in-process samples were taken, and subsequently poloxamer 188 and mannitol was added in amounts to reach the desired concentration in the final formulation. Previous studies (not shown) had revealed solubility issues if poloxamer 188 and mannitol was included in the buffer solution. Finally WFI was added to reach the final volume pH was adjusted with hydrochloric acid.

Final Formulations:

2.0, 3.3; 6.7; and 10 mg/ml growth hormone conjugate I 1.0 mg/ml poloxamer 188

0.68 mg/ml histidine 44 mg/ml mannitol 3.0 mg/ml phenol pH 6.3.

| | Phenol conc. of histidine and phenol solution | | |
|---|---|---|---|
| Sample | 5.0 mg/ml | 10 mg/ml | 30 mg/ml |
| In-process (to reach 2 mg/ml) | 4.1 | 6.7 | 77.3 |
| 2.0 mg/ml | 3.7 | 4.1 | 49.9 |
| In-process (to reach 3.3 mg/ml) | 3.6 | 4.6 | 31.0 |
| 3.3 mg/ml | 3.4 | 3.5 | 18.4 |
| In-process (to reach 6.7 mg/ml) | 3.7 | 3.9 | 8.0 |
| 6.7 mg/ml | 3.6 | 3.6 | 7.4 |
| In-process (to reach 10 mg/ml) | — | 3.8 | 8.3 |
| 10.0 mg/ml | — | 3.6 | 8.2 |

Table 2 shows the HMWP (%) in in-process samples and final formulations depending on starting phenol concentration and GH concentration. Initial HMWP level of conjugate I preparation was 3.7%. A very high HMWP content was obtained when a high concentration of phenol was mixed with a low concentration of growth hormone conjugate.

The invention claimed is:

1. A pharmaceutical composition comprising
5-10 mg/mL growth hormone albumin binder conjugate,
1-3 mg/mL poloxamer 188,
0.5-1.0 mg/mL histidine buffer,
40-45 mg/mL mannitol,
3-4 mg/mL phenol, and
pH of 6.5-7.0,
wherein the growth hormone conjugate is 2. A pharmaceutical composition comprising
5-10 mg/ml growth hormone albumin binder conjugate,
1.0 mg/mL poloxamer 188,
0.68 mg/mL histidine buffer,
44 mg/ml mannitol,
4 mg/mL phenol, and
pH of 6.8;

wherein the growth hormone conjugate is
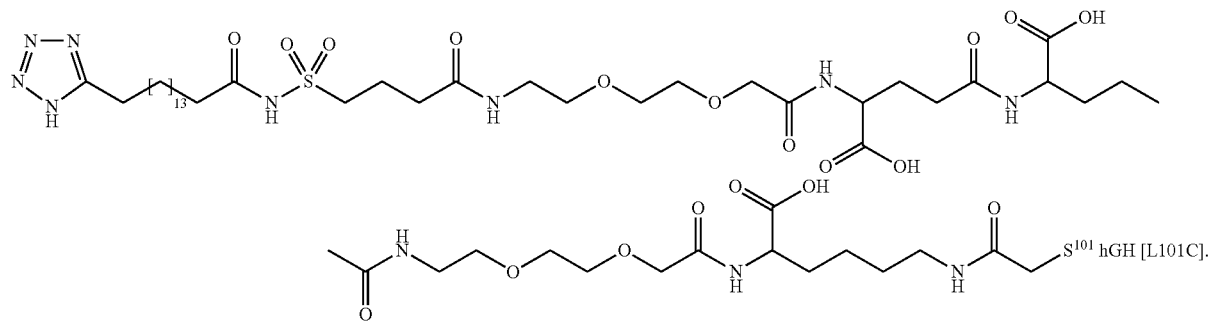
* * * * *